United States Patent [19]

Billington et al.

[11] Patent Number: 5,648,382

[45] Date of Patent: Jul. 15, 1997

[54] NEW CYCLOHEXANE COMPOUNDS

[75] Inventors: David Billington, Birmingham, Great Britain; Isabelle Picard, Paris, France; Ghanem Atassi, Saint-Cloud, France; Alain Pierre, Marly le Roi, France; Michaël Burbridge, Courbevoie, France; Nicolas Guilbaud, Paris, France

[73] Assignee: Adir et Compagnie, Courbevoie, France

[21] Appl. No.: 639,419

[22] Filed: Apr. 29, 1996

[30] Foreign Application Priority Data

Apr. 27, 1995 [FR] France .................. 95 05052

[51] Int. Cl.⁶ .................. C07D 303/02; A61K 31/335
[52] U.S. Cl. .................. 514/475; 549/332
[58] Field of Search .................. 549/332; 514/475

[56] References Cited

U.S. PATENT DOCUMENTS

| | | | |
|---|---|---|---|
| 3,651,007 | 3/1972 | Sigg et al. | 549/332 |
| 3,659,005 | 4/1972 | Sigg et al. | 549/332 |
| 5,204,345 | 4/1993 | Kishimoto et al. | 514/231.5 |

*Primary Examiner*—C. Warren Ivy
*Assistant Examiner*—Lyman H. Smith
*Attorney, Agent, or Firm*—The Firm of Gordon W. Hueschen

[57] ABSTRACT

Compounds of formula (I):

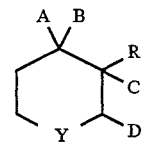

wherein:

R is selected from the radicals:

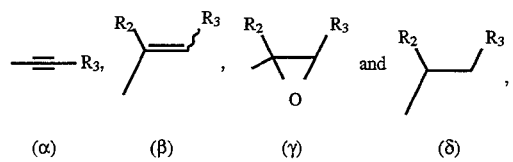

Y is selected from

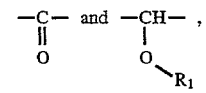

$R_1$ represents the radical

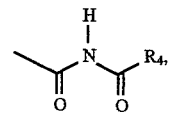

and A, B, C, D, $R_2$, $R_3$ and $R_4$ are as defined in the description, and also the possible geometric isomers and/or diastereoisomers and/or enantiomers thereof in pure form or in the form of a mixture. The compounds of the present invention have a therapeutic use as a result of their angiogenesis-inhibiting activity.

11 Claims, No Drawings

NEW CYCLOHEXANE COMPOUNDS

The present invention relates to new cyclohexane compounds, a process for their preparation and pharmaceutical compositions containing them. The compounds of the present invention have a very valuable therapeutic use as a result of their angiogenesis-inhibiting activity.

Angiogenesis (or neovascularization) is defined as the development and growth of new capillary blood vessels. The process of angiogenesis is essential in numerous physiological situations including the development of an embryo, normal healing of wounds and the development of the endometrium after menstruation. Apart from in those circumstances, angiogenesis in the normal adult is very rare and mitosis of the endothelial cells which generates the walls of blood vessels is very slow, with periods of cellular renewal measured in years.

Abnormal angiogenesis (that is to say stimulation of the growth of new blood vessels as a result of a pathological syndrome) is an established characteristic of numerous diseases, notably diabetic retinopathy, rheumatoid arthritis, haemangiomas and the growth of solid tumours. Angiogenesis may also play a significant part in other diseases, such as coronary artery disease.

In the field of oncology it has been demonstrated that the growth of solid tumours is entirely dependent on the constant development of new blood vessels, and that that development is correlated, for the metastases of certain cancers, with the growth size of the primary tumour (J. Folkman, *New Engl. Med.*, 285 (1971), 1182–1185).

A pharmaceutical treatment (that is to say using an angiogenesis inhibitor) may therefore stop the growth of primary tumours, impede or reduce the formation of metastases, impede the appearance of secondary growths. Such angiogenesis inhibitors are also useful in the treatment of the above-mentioned non-neoplasic disorders in which an angiogenic activity occurs.

Angiogenesis inhibitors are described in the literature. The prior art of the compounds of the present invention is illustrated especially by the patent specifications EP-A-357 061 and JP-A01-233 275, which describe fumagillol compounds (formula (A)) and ovalicine compounds (formula (B)) respectively:

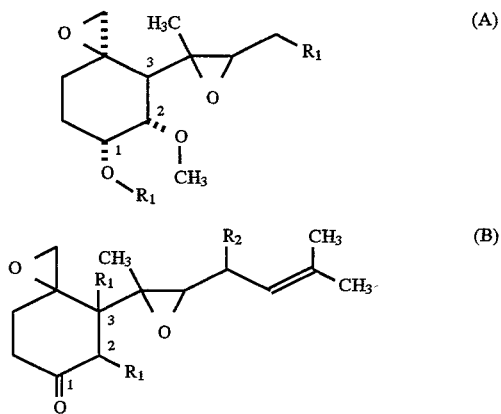

The compounds of the present invention differ from those of the prior art in that they are obtained entirely synthetically, thus allowing total control of the centres of asymmetry and enabling access to molecules that are completely novel as a result of substituents on the 2-carbon atom other than the methoxy group and also as a result of the groups carried by the 3-carbon atom being different from those described in formulae (A) and (B) described above.

Research into novel structures has been guided by the fact that therapeutic needs require the constant development of new angiogenesis-inhibiting compounds with the aim of obtaining active ingredients that are simultaneously more active, more specific and less toxic.

More especially, the present invention relates to compounds of the general formula (I):

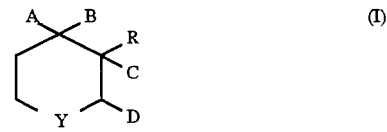

wherein:

R is selected from the radicals:

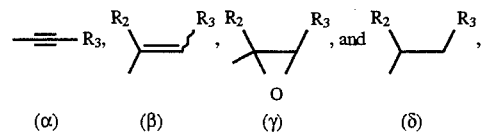

A and B are such that:

A represents a methyl radical and B represents an —OR$_1$ radical, or, and only when R represents the radical (δ), A represents hydrogen and B is selected from —CH$_2$—OH and —CH$_2$—OR$_1$ radicals, or A represents the radical

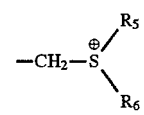

and B is selected from hydroxy and —OR$_1$ radicals, or

A and B, together with the carbon atom carrying them and with a group —CH$_2$—O—, form an oxirane ring, C and D are such that:

C represents a hydroxy radical and D is selected from hydrogen and bromine, or, and only when R represents the radical (δ), C represents an OR$_1$ radical and D is selected from hydrogen and bromine, or, and only when R represents the radical (δ), C and D each simultaneously represent hydrogen, or C and D, together with the carbon atoms carrying them and with a group —O—, form an oxirane ring or, together with the carbon atoms carrying them and with a group —O—CO—O—, form a dioxygenated heterocycle, or C and D together form a bond, Y is selected from —CO— and —CH(OR$_1$)— radicals, R$_1$ represents the radical

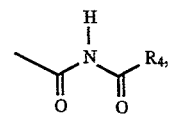

R$_2$ is selected from hydrogen, an optionally substituted alkyl radical and an optionally substituted aryl radical, R$_3$ is selected from hydrogen, an optionally substituted alkyl radical and an optionally substituted arylalkyl radical, R$_4$ is selected from an optionally substituted alkyl radical, an amino radical, an optionally substituted alkylamino radical, an optionally substituted dialkylamino radical, an optionally substituted aryl radical, an optionally substituted arylalkyl radical, an optionally substituted heteroarylalkyl radical and an optionally substituted alkenyl radical, $R_5$ represents an optionally substituted alkyl radical, $R_6$ is selected from an optionally substituted alkyl radical, an optionally substituted aryl radical, an optionally substituted arylalkyl radical, an optionally substituted heteroaryl radical and an optionally substituted heteroarylalkyl radical, it being understood that:

the alkyl chain in the terms "alkyl", "alkylamino", "dialkylamino", "arylalkyl" and "heteroarylalkyl" designates a saturated hydrocarbon chain containing from 1 to 6 carbon atoms in straight or branched chain, the term "aryl" designates a radical selected from phenyl and naphthyl, the term "heteroaryl" designates a radical selected from pyridyl, quinolyl, isoquinolyl, imidazolyl, indolyl and isoindolyl, the term "alkenyl" designates a radical selected from vinyl and isopropenyl, the term "optionally substituted" associated with the radicals alkyl, alkylamino, dialkylamino, aryl, arylalkyl, heteroaryl, heteroarylalkyl and alkenyl denotes that those radicals may optionally be substituted, in the acyclic moieties and/or, where applicable, in the cyclic moieties, by one or more chemical entities selected from:

hydroxy, halogen, selected from fluorine, chlorine, bromine and iodine, trihalomethyl, nitro, amino, alkylamino, dialkylamino straight-chained or branched alkoxy containing from 1 to 6 carbon atoms, carboxy, straight-chained or branched alkoxycarbonyl containing from 1 to 6 carbon atoms, and straight-chained or branched acyl containing from 1 to 6 carbon atoms, and also to the possible geometric isomers thereof, the possible diastereoisomers thereof and the possible enantiomers thereof in pure form or in the form of a mixture.

The present invention relates also to a process for the preparation of compounds of formula (I) which is characterised in that the compound of formula (II):

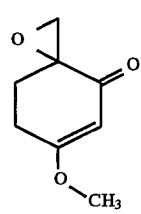
(II)

obtained in accordance with the method of operation described by E. J. Corey and J. P. Dittami, *J.A.C.S.*, (1985), 107, 256–257, is subjected, depending on the compound of formula (I) desired, to a combination of one or more of the following reactions:

a) For the Insertion of the Radical R as Defined for Formula (I), to the addition, in the presence of butyllithium, in an anhydrous polar solvent, such as toluene or ether, alone or in admixture, under an inert atmosphere, at a temperature of from −78° C. to 0° C., of a compound of formula (III) or of a compound of formula (IV):

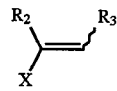 (III)

 (IV)

wherein $R_2$ and $R_3$ are as defined for formula (I) and X represents a halogen atom, to obtain a compound in which R represents (β) or (α), respectively, it being possible for the above-defined compounds in which R represents (α) or (β) to be subjected to catalytic hydrogenation to yield compounds in which R represents (δ) as defined for formula (I), it being possible for the compounds in which R represents (α) as defined for formula (I) to be subjected to the action of an oxidising agent, such as metachloroperbenzoic acid or dimethyldioxirane, to obtain compounds in which R represents (γ) as defined for formula (I), b) For the Radical Y Defined for Formula (I), to conversion of the methoxy function of the compound of formula (II) into the ketone function on insertion of the radical R described above, it being possible, if desired, for the compounds in which Y represents —CO— to be subjected to the action of a reducing agent, such as sodium borohydride, to obtain the corresponding alcohol, which is subjected to the action of an isocyanate of formula (V):

 (V)

wherein $R_4$ is as defined for formula (I), so as to obtain compounds in which Y represents —CH(OR$_1$)—, $R_1$ being as defined for formula (I), c) For the Various Meanings of A and B, for compounds of formula (I) in which A and B, together with the carbon atom carrying them and with a —CH$_2$—O— group, form an oxirane ring, without any conversion, that oxirane ring already being present in the starting material of formula (II) defined above, for compounds of formula (I) in which A represents a methyl radical and B represents an —OR$_1$ radical, to reaction of the oxirane ring present in the above-defined compound of formula (II) in accordance with the following reaction:

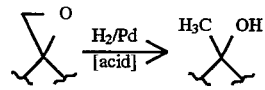

for compounds of formula (I) in which R represents the radical (δ) defined above, A represents hydrogen and B is selected from —CH$_2$—OH and —CH$_2$—OR$_1$ radicals, to reaction of the oxirane ring present in formula (II) defined above in accordance with the following reactions:

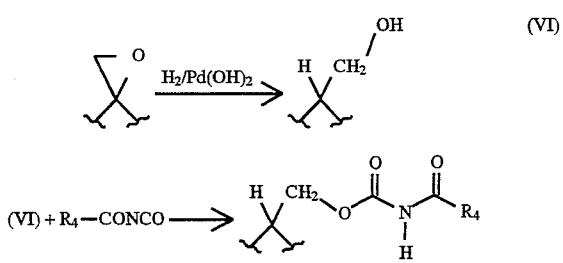

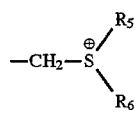

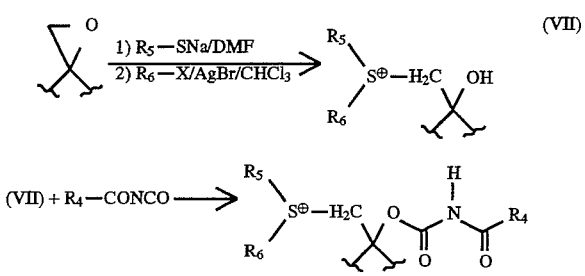

wherein $R_4$ is as defined for formula (I), for compounds of formula (I) in which A represents the radical $$-CH_2-\overset{\oplus}{S}\diagdown_{R_6}^{R_5}$$

and B is selected from hydroxy and $-OR_1$ radicals, to reaction of the oxirane ring present in formula (II) defined above in accordance with the following reactions:

wherein $R_4$, $R_5$ and $R_6$ are as defined for formula (I), and X represents a halogen atom, d) For the Various Meanings of C and D, for compounds of formula (I) in which C represents a hydroxy radical and D represents bromine, to reaction with a brominating agent, such as N-bromo-succinimide, of the synthesis intermediate of formula (VIII) obtained on insertion of the radical R (see paragraph a) above), in accordance with the following reaction:

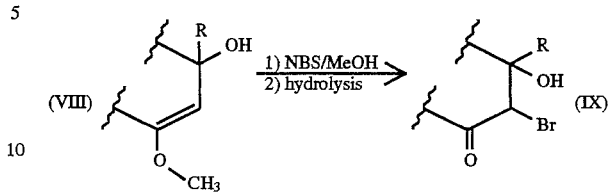

wherein R is as defined above, for compounds of formula (I) wherein C represents a hydroxy radical and D represents hydrogen, to reaction of the synthesis intermediate of formula (VIII) defined above in accordance with the following reaction:

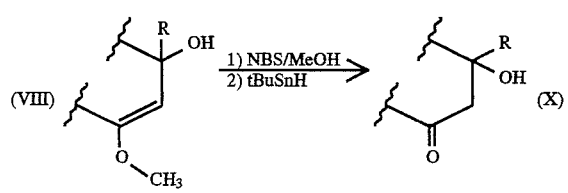

wherein R is as defined above, it being possible for the hydroxy functions of the compounds of formulae (IX) and (X) defined above to be carbamoylated by the action of an isocyanate of formula $R_4$—CONCO, $R_4$ being as defined above, to obtain compounds of formula (I) in which D is selected from hydrogen and bromine and C represents the radical $OR_1$, compounds of formula (I) in which the meanings of C and D are other than those defined above being obtained from the compound of formula (VIII) in accordance with the following scheme:

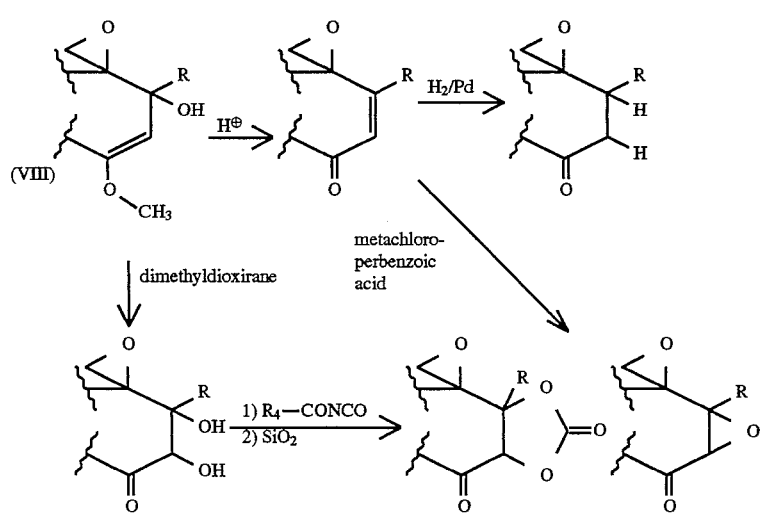

wherein R and $R_4$ are as defined above, it being possible for the totality of the synthesis intermediates and also the compounds of formula (1) optionally to be purified by a conventional method of purification and separated, if desired and where applicable, into geometric isomers and/or diastereoisomers and/or enantiomers by a conventional method of separation.

Compounds of formula (I) wherein C and D, together with the carbon atoms carrying them and with a group —O—, form an oxirane ring, may also be obtained in accordance with the following reaction:

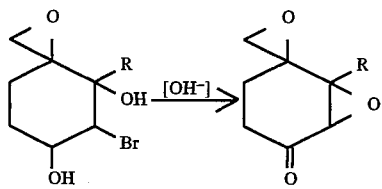

wherein R is as defined above,

Compounds of formula (I) wherein R represents the radical (δ) as defined above may advantageously be obtained by the action, on the compound of formula (II) defined above, of a compound of formula (XI):

wherein $R_2$ and $R_3$ are as defined above, in the presence of cerium(III) chloride, in tetrahydrofuran, at an appropriate temperature, for example −78° C.

The various reactions described in the process explained above shall be carried out in a chemically suitable order determined by the person skilled in the art in the light of the Examples described hereinafter in the description. Generally, the radical R will be introduced at the beginning of the synthesis and the carbamoylation reactions will be carried out in the course of the last stages of the synthesis.

The compounds of formula (I) have valuable pharmacological properties. Indeed those compounds are powerful angiogenesis inhibitors that have the advantage of exhibiting a far lower toxicity than the reference compounds. They therefore have an excellent therapeutic index.

Those compounds are consequently used therapeutically as anti-tumour agents, in the inhibition of the formation and growth of metastases, and also in the treatment of diabetic retinopathy, rheumatoid arthritis, haemangiomas and coronary artery diseases and, more generally, in conditions resulting from or associated with angiogenesis disorders.

The present invention relates also to pharmaceutical compositions comprising compounds of formula (I), their possible geometric isomers and/or diastereoisomers and/or enantiomers in pure form or in the form of a mixture, alone or in combination with one or more inert non-toxic excipients or carriers.

Among the pharmaceutical compositions according to the invention there may be mentioned more especially those which are suitable for oral, parenteral, nasal, rectal, perlingual, transdermal, ocular or respiratory administration, and especially tablets or dragées, sublingual tablets, gelatin capsules, suppositories, creams, ointments, dermal gels, patches, injectable or drinkable preparations, aerosols and eye or nose drops.

The useful dosage varies according to the age and weight of the patient, the administration route, the nature of the therapeutic indication and possible associated treatments, and ranges from 0.01 to 1 g per day taken in one or more doses.

The following Examples illustrate the invention but do not limit it in any way. The starting materials are known or are prepared by known method of operations.

EXAMPLE 1

(3S*,4S*,5R*,6R*)-5-Bromo-6-chloroacetylcarbamoyloxy-4-hydroxy-4-(1-methylpropen-1-yl)-1-oxa-spiro[2.5]octane

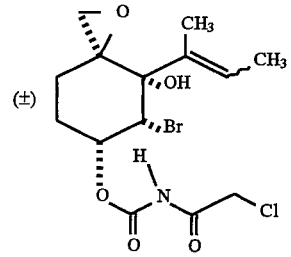

Step A: 4-Hydroxy-6-methoxy-4-(1-methylpropen-1-yl)-1-oxa-spiro[2.5]oct-5-ene 54 ml of tert-butyllithium (1.7M in pentane, that is 91.89 mmol) are added dropwise under a nitrogen atmosphere to a solution, cooled to −78° C., of 4.62 ml (45.41 mmol) of (cis, trans)-2-bromo-2-butene in 140 ml of anhydrous diethyl ether. The whole is then stirred at −78° C. for 5 minutes and subsequently at 0° C. for 1 hour. There is then added dropwise to that solution a solution, cooled to −78° C., of 6-methoxy-1-oxa-spiro[2.5]oct-5-en-4-one, prepared in accordance with the method of operation described by E. J. Corey and J. P. Dittami, (J. A. C. S. (1985), 107, 256–257) (4 g; 25.94 mmol) in 40 ml of anhydrous toluene. After 1 hour's stirring at −78° C., the reaction mixture is poured into an aqueous 10% ammonium chloride solution (400 ml). The whole is diluted with diethyl ether (400 ml) and the reaction mixture is extracted. Conventional treatment of the organic phase yields an oily residue which is chromatographed on silica gel (eluant: pentane/ethyl acetate, 7:1) to obtain 3.4 g (16.17 mmol) of the expected product.

Yield: 60%

Step B: 5-Bromo-6,6-dimethoxy-4-hydroxy-4-(1-methylpropen-1-yl)-1-oxa-spiro[2.5]octane 3.4 g (19.32 mmol) of N-bromosuccinimide are added to a solution, cooled to 0° C., of 3.4 g (16.17 mmol) of the compound obtained in Step A in 160 ml of methanol. After 15 minutes' stirring at 0° C., the reaction mixture is evaporated. The oily residue is taken up in ethyl acetate. After treatment of the organic phase and purification on silica gel (eluant: pentane/ethyl acetate 8:1), 3.2 g (9.96 mmol) of the expected product are obtained.

Yield: 62%

Step C: 5-Bromo-4-hydroxy-4-(1-methylpropen-1-yl)-1-oxa-spiro[2.5]octan-6-one 1.9 g (9.96 mmol) of para-toluenesulphonic acid are added at room temperature to a solution of 3.2 g (9.96 mmol) of the compound obtained in Step B in 120 ml of an acetone/water mixture (3:2). When the reaction, followed by thin-layer chromatrography, is complete, the acetone is evaporated off. The aqueous phase remaining is then extracted with ethyl acetate (200 ml). After conventional treatment of the organic phase, 2.23 g (8.1 mmol) of the expected product are obtained.

Yield: 81%

Step D: 5-Bromo-4,6-hydroxy-4-(1-methylpropen-1-yl)-1-oxa-spiro[2.5]octane 137 mg (3.6 mmol) of sodium borohydride are added in small portions, at room temperature, to a solution of 1 g (3.63 mmol) of the compound obtained in Step C in 110 ml of a dichloromethane/methanol mixture (10:1). When the reaction, followed by thin-layer chromatography, is complete, the reaction mixture is concentrated, taken up in methanol, and then reconcentrated. After chromatography on silica gel (eluant: pentane/ethyl acetate, 4:1), 0.46 g (1.66 mmol) of the expected product is obtained.

Yield: 46%

Step E: (3S*,4S*,5R*,6R*)-5-Bromo-6-chloroacetylcarbamoyloxy-4-hydroxy-4-(1-methylpropen-1-yl)-1-oxa-spiro[2.5]octane 0.26 ml (3.087 mmol) of chloroacetyl isocyanate is added dropwise, under a nitrogen atmosphere, to a solution, cooled to 0° C., of 0.46 g (1.66 mmol) of the compound obtained in Step D in 10 ml of anhydrous dichloromethane. After 30 minutes' stirring at 0° C., 10 ml of water are poured into the reaction mixture and the whole is stirred for 1 hour. After conventional treatment of the organic phase, 0.46 g (1.16 mmol) of the expected compound is obtained in the form of a mousse.

Yield: 70%

EXAMPLE 2

(3S*,4R*,5R*,6R*)-5-Bromo-6-chloroacetylcarbamoyloxy-4-hydroxy-4-(2,3-dimethyloxiran-2-yl)-1-oxa-spiro[2.5]octane

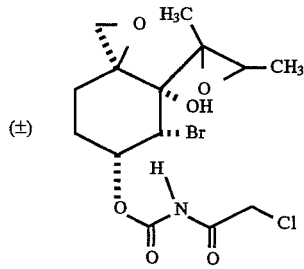

1.12 g (4.74 mmol) of 72% 3-chloroperbenzoic acid are added to a solution of 0.46 g (1.16 mmol) of the compound obtained in Example 1 in 30 ml of dichloromethane. The reaction mixture is stirred at room temperature for 5 hours. The solid formed during the course of the reaction is filtered off. After conventional treatment of the organic phase and purification by chromatography on silica gel twice (eluant: hexane/ethyl acetate, 3:2), 0.146 mg (0.354 mmol) of the expected compound is obtained in the form of a mousse.

Yield: 48%

Elemental analysis:
(Empirical formula: $C_{14}H_{19}BrClNO_6$ molecular weight: 412.66)

|              | C     | H    | N    | Br    | Cl   |
|--------------|-------|------|------|-------|------|
| % found      | 40.76 | 4.78 | 3.42 | 19.00 | 8.00 |
| % calculated | 40.75 | 4.64 | 3.39 | 19.36 | 8.60 |

EXAMPLE 3

(3S*,4S*,5R*,6R*)-5-Bromo-6-chloroacetylcarbamoyloxy-4-hydroxy-4-(propen-2-yl)-1-oxa-spiro[2.5]octane

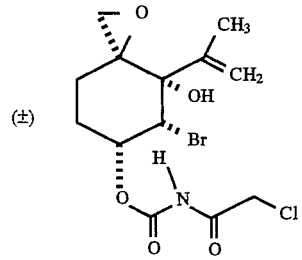

Step A: 4-Hydroxy-6-methoxy-4-(propen-2-yl)-1-oxa-spiro[2.5]-5-oct-5-ene

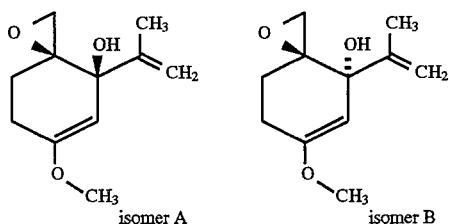

isomer A    isomer B

By proceeding in accordance with the method of operation described in Step A of Example 1, starting from 9.2 ml (0.104 mol) of 2-bromo-1-propene, 115 ml of tert-butyllithium (1.7M in pentane, that is 0.196 mol) in 335 ml of anhydrous diethyl ether and 7.88 g (51.2 mmol) of 6-methoxy-1-oxa-spiro[2.5]oct-5-en-4-one in 80 ml of anhydrous toluene, 0.94 g (4.79 mmol) of isomer A and 5.82 g (19.24 mmol) of isomer B are obtained after chromatography on silica gel (eluant: pentane/ethyl acetate, 7:1).

Yield: 67%

Step B: 5-Bromo-6,6-dimethoxy-4-hydroxy-4-(propen-2-yl)-1-oxa-spiro[2.5]octane

By proceeding in accordance with the method of operation described in Step B of Example 1, starting from 8.37 g (42.67 mmol) of isomer B obtained in Step A and 8.25 g (46.97 mmol) of N-bromosuccinimide in 420 ml of methanol, 10.01 g (32.52 mmol) of the expected compound are obtained after chromatography on silica gel twice (eluant: petroleum ether/ethyl acetate, 9:1).

Yield: 76%

Step C: 5-Bromo-4-hydroxy-4-(propen-2-yl)-1-oxa-spiro[2.5]octan-6-one

By proceeding in accordance with the method of operation described in Step C of Example 1, starting from 4.58 g (14.89 mmol) of the compound obtained in Step B and 4.25 g (22.33 mmol) of para-toluenesulphonic acid in 400 ml of an acetone/water mixture (3:2), 3.54 g (13.56 mmol) of the expected compound are obtained.

Yield: 91%

Step D: 5-Bromo-4,6-hydroxy-4-(propen-2-yl)-1-oxa-spiro[2.5]octane

By proceeding in accordance with the method of operation described in Step D of Example 1, starting from 4.34 g (16 mmol) of the compound obtained in Step C and 0.64 g (16 mmol) of sodium borohydride in 550 ml of a dichloromethane/methanol mixture (10:1), 3.2 g (12.16 mmol) of the expected compound are obtained.

Yield: 73%

Step E: (3S*,4S*,5R*,6R*)-5-Bromo-6-chloroacetylcarbamoyloxy-4-hydroxy-4-(propen-2-yl)-1-oxa-spiro[2.5]octane By proceeding in accordance with the method of operation described in Step E of Example 1, starting from 1.03 g (3.9 mmol) of the compound obtained in Step D and 0.62 ml (7.3 mmol) of chloroacetyl isocyanate in 20 ml of anhydrous dichloromethane, 2.14 g (5.6 mmol) of the expected compound are obtained.

EXAMPLE 4

(3S*,4S*,5R*,6R*)-5-Bromo-6-chloroacetylcarbamoyloxy-4-hydroxy-4-(2-methyl-2-oxiranyl)-1-oxa-spiro[2.5]octane

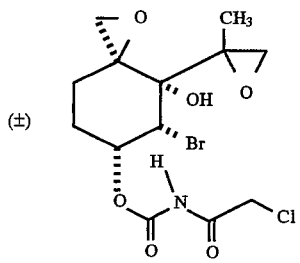

By proceeding in accordance with the method of operation described in Example 2, starting from 2.14 g (5.6 mmol) of the crude compound obtained in Example 3 and 1.93 g (11.2 mmol) of 72% 3-chloroperbenzoic acid in 55 ml of dichloromethane, 0.9 g (2.26 mmol) of a mixture of the two expected diastereoisomers (73/27) is obtained in the form of a mousse after chromatography on silica gel twice (eluant: hexane/ethyl acetate, 3:1).

Yield: 84%

Elemental analysis:
(Empirical formula: $C_{13}H_{17}BrClNO_6$ molecular weight: 398.64)

|  | C | H | N | Br | Cl |
|---|---|---|---|---|---|
| % found | 40.30 | 4.20 | 3.67 | 19.00 | 9.50 |
| % calculated | 39.17 | 4.30 | 3.51 | 20.04 | 8.89 |

EXAMPLE 5

(3S*,4S*,6R*)-6-Chloroacetylcarbamoyloxy-4-hydroxy-4-(1-methyl-propen-1-yl)-1-oxa-spiro[2.5]octane

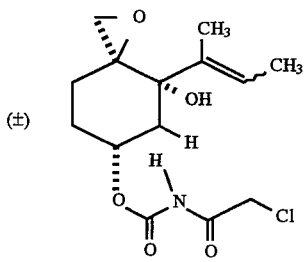

Step A: 4,6-Hydroxy-4-(1-methylpropen-1-yl)-1-oxa-spiro[2.5]octane 1.8 ml (6.78 mmol) of tributyltin hydride are added to a solution of 0.94 g (3.39 mmol) of the compound obtained in Example 1, Step D in 35 ml of anhydrous toluene. The reaction mixture is subjected to stirring and heated to reflux. When the reaction, followed by thin-layer chromatography, is complete, the mixture is cooled and then evaporated. The oily residue is taken up in ethyl acetate, and 3 g of potassium fluoride in 15 ml of water are added. After 15 minutes' stirring, the tributyltin fluoride formed is filtered off. After conventional treatment of the organic phase and purification by chromatography on silica gel (eluant: pentane/ethyl acetate, 2:1), 0.32 g (1.61 mmol) of the expected trans compound and 0.31 g (1.56 mmol) of the expected cis compound are obtained.

Yield: 94%

Step B: (3S*, 4S*, 6R*)-6-Chloroacetylcarbamoyloxy-4-hydroxy-4-(1-methyl-propen-1-yl)-1-oxa-spiro[2.5]octane By proceeding in accordance with the method of operation described in Step E of Example 1, starting from 0.32 g (1.61 mmol) of the trans compound obtained in Step A and 0.245 ml (2.91 mmol) of chloroacetyl isocyanate in 10 ml of anhydrous dichloromethane, 0.5 g (1.57 mmol) of the expected compound is obtained.

Yield: 97%

EXAMPLE 6

(3S*, 4R*, 6R*)-6-Chloroacetylcarbamoyloxy-4-hydroxy-4-(2,3-dimethyloxiran-2-yl)-1-oxa-spiro[2.5]octane (trans isomer)

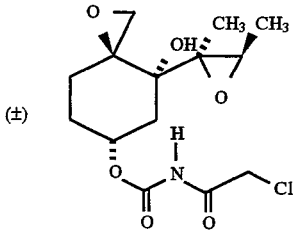

By proceeding in accordance with the method of operation described in Example 2, starting from 0.5 g (1.57 mmol) of the compound obtained in Example 5 and 0.38 g (3.14 mmol) of 72% 3-chloroperbenzoic acid in 25 ml of dichloromethane, 0.33 g (0.99 mmol) of the expected compound are obtained after chromatography on silica gel (eluant: heptane/ethyl acetate, 1:1).

Yield: 63%

Elemental analysis:
(Empirical formula: $C_{14}H_{20}ClNO_6$ molecular weight: 333.77)

|  | C | H | N | Cl |
|---|---|---|---|---|
| % found | 50.88 | 6.45 | 4.01 | 10.45 |
| % calculated | 50.38 | 6.04 | 4.20 | 10.62 |

EXAMPLE 7

(3S*; 4R*, 6R*)-6-Chloroacetylcarbamoyloxy-4-hydroxy-4-(2,3-di-methyl-2-oxiranyl)-1-oxa-spiro[2.5]octane (cis isomer)

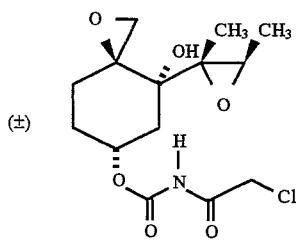

By proceeding in accordance with the method of operation described in Example 6 starting from the cis isomer obtained in Step A of Example 5, treated in accordance with the method of operation described in Step B of Example 5, 0.145 g (0.43 mmol) of the expected compound is obtained.

Yield: 64%

Elemental analysis:
(Empirical formula: $C_{14}H_{20}ClNO_6$ molecular weight 333.77)

|  | C | H | N | Cl |
|---|---|---|---|---|
| % found | 50.73 | 6.40 | 4.13 | 10.76 |
| % calculated | 50.38 | 6.04 | 4.20 | 10.62 |

EXAMPLE 8

(3S*, 4S*, 6R*)-6-Chloroacetylcarbamoyloxy-4-hydroxy-4-(propen-2-yl)-1-oxa-spiro[2.5]octane

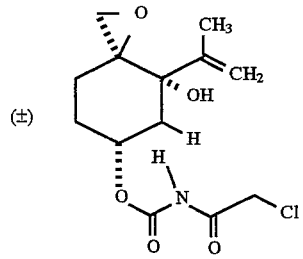

Step A: 4,6-Hydroxy-4-(propen-2-yl)-1-oxa-spiro[2.5]octane

By proceeding in accordance with the method of operation described in Step A of Example 5, starting from 2.16 g (8.2 mmol) of the compound obtained in Step D of Example 3 and 4.4 ml (16.4 mmol) of tributyltin hydride in 85 ml of anhydrous toluene, 1.74 g (9.44 mmol) of the expected crude compound are obtained.

Step B: (3S*, 4S*, 6R*)-6-Chloroacetylcarbamoyloxy-4-hydroxy-4-(propen-2-yl)-1- oxa-spiro[2.5]octane By proceeding in accordance with the method of operation described in Step E of Example 1, starting from 1.74 g (9.44 mmol) of the crude compound obtained in the preceding Step and 1.5 ml (17.6 mmol) of chloroacetyl isocyanate in 45 ml of anhydrous dichloromethane, 1.87 g (6.15 mmol) of the expected compound are obtained.

EXAMPLE 9

(3S*, 4S*, 6R*)-6-Chloroacetylcarbamoyloxy-4-hydroxy-4-(2-methyloxiran-2-yl)-1-oxa-spiro[2.5]octane

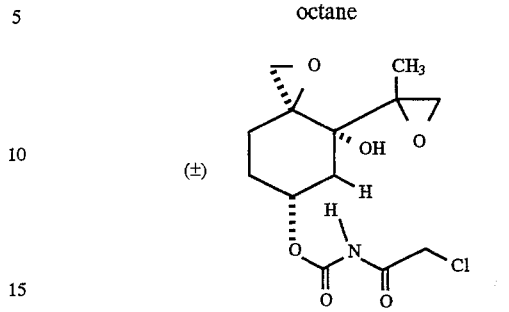

By proceeding in accordance with the method of operation described in Example 2, starting from 1.66 g (5.5 mmol) of the compound obtained in Example 8 and 1.9 g (11.0 mmol) of 72% 3-chloroperbenzoic acid in 60 ml of dichloromethane, 1.4 g (4.38 mmol) of the expected compound are obtained in the form of a mousse after chromatography on silica gel twice (eluant: hexane/ethyl acetate, 3:2).

Yield: 80%

Elemental analysis:
(Empirical formula: $C_{13}H_{18}ClNO_6$ molecular weight: 319.74)

|  | C | H | N | Cl |
|---|---|---|---|---|
| % found | 48.73 | 5.79 | 4.42 | 11.53 |
| % calculated | 48.83 | 5.67 | 4.38 | 11.09 |

EXAMPLE 10

(3S*, 4S*, 5R*, 6R*)-5-Bromo-6-chloroacetylcarbamoyloxy-4-hydroxy-4-(5-phenylpentyl)-1-oxa-spiro[2.5]octane

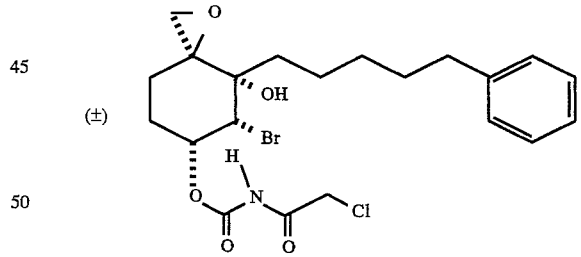

Step A: 5-Bromo-4-hydroxy-4-(5-phenylpentyl)-1-oxa-spiro[2.5]octan-6-one 74 ml (0.118 mol) of n-butyllithium (1.6 molar in hexane) are added dropwise, under a nitrogen atmosphere, to a solution, cooled to −78° C., of 25 ml (0.157 mol) of 5-phenylpentyne in 400 ml of anhydrous diethyl ether. The whole is stirred at −78° C. for 15 minutes and then at 0° C. for 75 minutes. There is then added dropwise to that solution a solution, cooled to −78° C., of 6-methoxy-1-oxa-spiro[2.5] oct-5-en-4-one (11 g; 71.33 mmol) in 80 ml of anhydrous toluene. After 1 hour's stirring at −78° C., the reaction mixture is poured into an aqueous 10% ammonium chloride solution (1000 ml). Conventional treatment of the organic phase yields 22 g (74 mmol) of 4-hydroxy-6-methoxy-4-(5- phenylpenten-1-yl)-1-oxa-spiro[2.5]octene (2 isomers) in the form of an oily residue which is used in the following step without being purified. Hydrogenation of a solution of 22 g (74 mmol) of that mixture of isomers in 610 ml of benzene in the presence of 10 g of Lindlar catalyst for a period of 7 hours results, after filtration and evaporation, in 22 g (73 mmol) of 4-hydroxy-6methoxy-4-(5-phenylpentyl)-1-oxa-spiro[2.5]oct-5-ene in the form of an oily residue which is used in the following step without being purified.

13.94 g (78.32 mmol) of N-bromosuccinimide are added to a solution, cooled to 0° C., of 22 g (73 mmol) of the above mixture in 100 ml de methanol. After 30 minutes' stirring at 0° C., the reaction mixture is evaporated. The oily residue is taken up in ethyl acetate. After conventional treatment of the organic phase and purification on silica gel (eluant: heptane/ethyl acetate, 3:1), 5 isomers are obtained in the following proportions: 8.62 g (20.85 mmol) of isomer A, 5.19 g (12.55 mmol) of isomer B, 6.89 g (16.67 mmol) of a mixture of isomers C and E and 3.1 g (7.5 mmol)of isomer D.

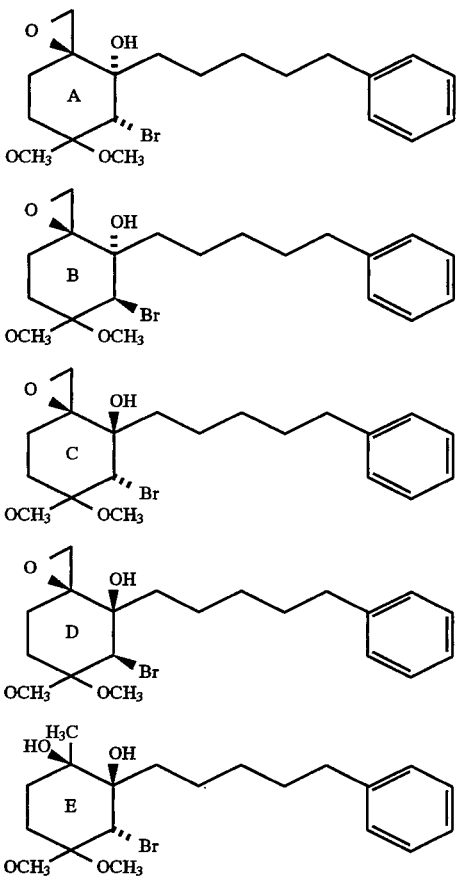

By proceeding in accordance with the method of operation described in Step C of Example 1, starting from 8.62 g (20.9 mmol) of isomers A, B, C or D and 4 g (21 mmol) of para-toluenesulphonic acid in 250 ml of an acetone/water mixture (3:2), 5.06 g (13.78 mmol) of the expected compound are obtained.

Yield: 66%

Step B: 5-Bromo-4,6-hydroxy-4-(5-phenylpentyl)-1-oxa-spiro[2.5]octane

By proceeding in accordance with the method of operation described in Step D of Example 1, starting from 5.06 g (13.78 mmol) of the compound obtained in the above Step and 0.29 g (7.66 mmol) of sodium borohydride in 550 ml of a dichloromethane/methanol mixture (10:1), 3.85 g (10.42 mmol) of the expected compound are obtained after chromatography on silica gel (eluant: pentane/ethyl acetate, 4:1).

Yield: 76%

Step C: 5-Bromo-6-chloroacetylcarbamoyloxy-4-hydroxy-4-(5-phenylpentyl)-1-oxa-spiro[2.5]octane By proceeding in accordance with the method of operation described in Step E of Example 1, starting from 1 g (2.7 mmol) of the compound obtained in the above Step and 0.42 ml (5.03 mmol) of chloroacetyl isocyanate in 30 ml of anhydrous dichloromethane, 0.497 g (1.017 mmol) of the expected compound is obtained after chromatography on silica gel (eluant: heptane/ethyl acetate, 5:2).

Yield: 38%

Elemental analysis:
(Empirical formula: C₂₁H₂₇BrClNO₅ molecular weight: 488.81)

|             | C     | H    | N    | Cl    | Br   |
|-------------|-------|------|------|-------|------|
| % found     | 53.07 | 5.58 | 2.93 | 6.00  | 8.00 |
| % calculated| 51.60 | 5.57 | 2.87 | 16.35 | 7.2  |

EXAMPLE 11

(3S*,4R*,6S*)-6-Chloroacetylcarbamoyloxy-4-hydroxy-4-(5-phenylpentyl)-1-oxa- spiro[2.5]octane

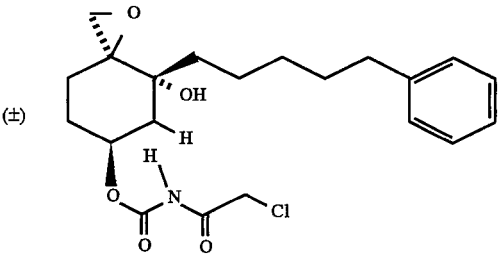

Step A: (3S*,4R*,6S*)-4,6-Hydroxy-4-(5-phenylpentyl)-1-oxa-spiro[2.5]octane

By proceeding in accordance with the method of operation described in Step A of Example 5, starting from 1.02 g (2.77 mmol) of isomer C obtained in Step B of Example 10 and 1.2 ml (4.52 mmol) of tributyltin hydride in 25 ml of anhydrous toluene, 0.54 g (1.86 mmol) of the expected compound is obtained after chromatography on silica gel (eluant: pentane/ethyl acetate, 3:1).

Yield: 67%

Step B: (3S*,4R*,6S*)-6-Chloroacetylcarbamoyloxy-4-hydroxy-4-(5-phenylpentyl)-1-oxa-spiro[2.5]octane By proceeding in accordance with the method of operation described in Step E of Example 1, starting from 0.54 g (1.86 mmol) of the compound obtained in the above Step and 0.29 ml (3.5 mmol) of chloroacetyl isocyanate in 18 ml of anhydrous dichloromethane, followed by purification by chromatography on silica gel (eluant: heptane/ethyl acetate, 2:1), 0.24 g (0.59 mmol) of the expected compound and 0.38 g (0.72 mmol) of the compound of Example 12 are obtained.

Yield: 32%

Elemental analysis:

(Empirical formula: $C_{21}H_{28}ClNO_5$ molecular weight: 409.91)

| | C | H | N |
|---|---|---|---|
| % found | 62.79 | 7.18 | 3.32 |
| % calculated | 61.53 | 6.89 | 3.42 |

EXAMPLE 12

(3S; 4R*, 6S*)-4,6-Dichloroacetylcarbamoyloxy-4-(5-phenylpentyl)-1-oxa-spiro[2.5]octane

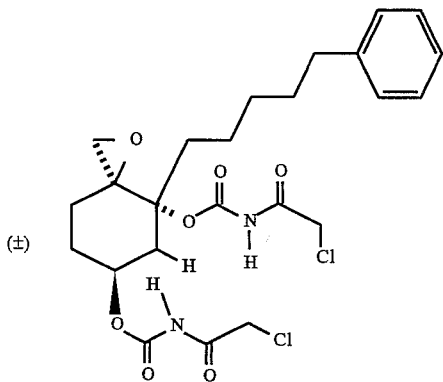

This dicarbamoylated compound is obtained by following the method of operation described in Example 11.

Yield: 39%

Elemental analysis:

(Empirical formula: $C_{24}H_{30}Cl_2N_2O_7$ molecular weight: 529.42)

| | C | H | N |
|---|---|---|---|
| % found | 54.25 | 5.94 | 5.47 |
| % calculated | 54.45 | 5.71 | 5.29 |

EXAMPLE 13

(3S*,4R*,5S*,6S*)-5-Bromo-6-chloroacetylcarbamoyloxy-4-hydroxy-4-[3-(3-phenylpentyl)oxiran-2-yl]-1-oxa-spiro[2.5]octane

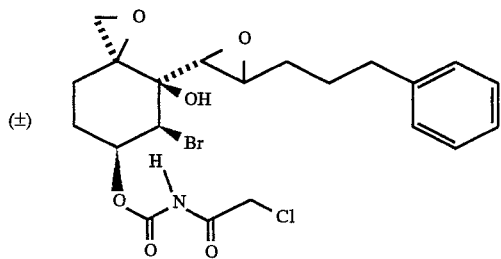

Step A: 5-bromo-4-hydroxy-4-(5-phenylpenten-1-yl)-1-oxa-spiro[2.5]octan-6-one

The hydrogenation of a solution of 4-hydroxy-6-methoxy-4-(5-phenylpentyn-1-yl)-1-oxa-spiro[2.5]octene, a crude mixture of isomers obtained in accordance with the method of operation described in Step A of Example 10 (10.67 g; 35.52 mmol), in 300 ml of benzene in the presence of 5 g of Lindlar catalyst for 1 hour yields, after filtration and evaporation, 10.67 g (35.5 mmol) of 4-hydroxy-6-methoxy-4-(5-phenylpenten-1-yl)-1-oxa-spiro[2.5]oct-5-ene (2 isomers) in the form of an oily reside which is used in the following step without being purified. 7.58 g (42.6 mmol) of N-bromosuccinimide are added to a solution, cooled to 0° C., of 10.67 g (35.5 mmol) of the above mixture in 360 ml of methanol. After 15 minutes' stirring at 0° C., the reaction mixture is evaporated. The oily residue is taken up in ethyl acetate. After treatment of the organic phase with water and purification by chromatography on silica gel (eluant: heptane/ethyl acetate, 5:1), 2 isomers are obtained in the following poroportions: 1.5 g (3.65 mmol) of isomer A and 3.14 g (7.63 mmol) of isomer B.

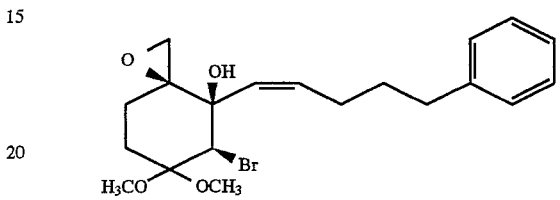

isomer A

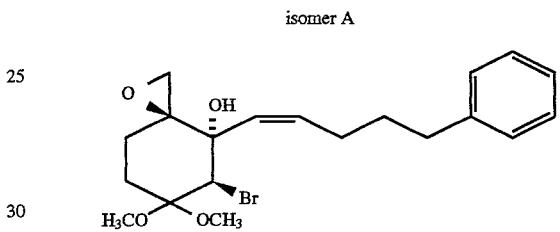

isomer B

By proceeding in accordance with the method of operation described in Step C of Example 1, starting from 1.5 g (3.65 mmol) of isomer A obtained above and 0.84 g (4.4 mmol) of para-toluenesulphonic acid in 125 ml of an acetone/water mixture (3:2), 0.9 g (2.46 mmol) of the expected compound is obtained after chromatography on silica gel (eluant: toluene/ethyl acetate, 9:1).

Yield: 78%

Step B: 5-Bromo-4,6-hydroxy-4-(5-phenylpenten-1-yl)-1-oxa-spiro[2.5]-octane

By proceeding in accordance with the method of operation described in Step D of Example 1, starting from 0.9 g (2.46 mmol) of the compound obtained in Step A and 45 mg (1.19 mmol) of sodium borohydride in 100 ml of a dichloromethane/methanol mixture (10:1), 0.26 g (0.71 mmol) of the expected compound is obtained after chromatography on silica gel (eluant: pentane/ethyl acetate, 3:1).

Yield: 21%

Step C: 5-Bromo-4,6-hydroxy-4-[3-(3phenylpentyl)oxiran-2-yl]-1-oxa-spiro[2.5]octane 0.26 g (0.71 mmol) of the compound obtained in the preceding Step are dissolved in 30 ml of dimethyldioxirane cooled to –20° C. The reaction mixture is stirred for several hours from –20° C. to room temperature and then concentrated. The oily residue obtained is chromatographed on silica gel (eluant: pentane/ethyl acetate, 4:1). 26 mg (0.068 mmol) of diastereoisomer A and 93 mg (0.24 mmol) of diastereoisomer B are obtained.

Yield: 44%

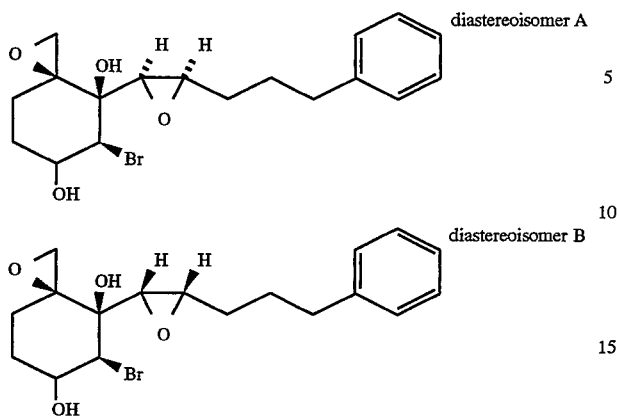

Step D: (3S*,4R*,5S*,6S*)-5-Bromo-6-chloroacetylcarbamoyloxy-4-hydroxy-4-[3-(3-phenyl-pentyl)-oxiran-2-yl]-1-oxa-spiro[2.5]octane By proceeding in accordance with the method of operation described in Step E of Example 1, starting from 93 mg (0.24 mmol) of the compound obtained in the above Step C and 40 ml (0.45 mmol) of chloroacetyl isocyanate in 5 ml of anhydrous dichloromethane, 50 mg(0.1 mmol) of the expected compound are obtained after chromatography on silica gel (eluant: heptane/ethyl acetate, 1.2:1).

Yield: 41%

Elemental analysis:
(Empirical formula: C₂₁H₂₈BrClNO₆ molecular weight: 502.79)

|  | C | H | N |
|---|---|---|---|
| % found | 50.47 | 5.12 | 2.84 |
| % calculated | 50.17 | 5.01 | 2.79 |

EXAMPLE 14

6-Chloroacetylcarbamoyloxy-4-(β-styryl)-1-oxa-spiro[2.5]oct-4-ene

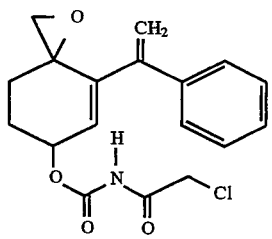

Step A: 4-(β-styryl)-1-oxa-spiro[2.5]oct-4-en-6-one

By proceeding in accordance with the method of operation described in Step A of Example 1, starting from 1.7 ml (13 mmol) of β-bromostyrene, 15.3 ml of tert-butyl-lithium (1.7M in pentane, that is 26 mmol) in 40 ml of anhydrous diethyl ether and 1 g (6.5 mmol) of 6-methoxy-1-oxa-spiro [2.5]oct-5-en-4-one in 10 ml of anhydrous toluene, 0.24 g (0.93 mmol) of isomer A, 0.42 g (1.63 mmol) of isomer B and 0.18 g (0.8 mmol) of the expected product are obtained after chromatography on silica gel twice (eluants: pentane/ethyl acetate, 5:1 and toluene/ethyl acetate, 95:5).

Yield: 12%

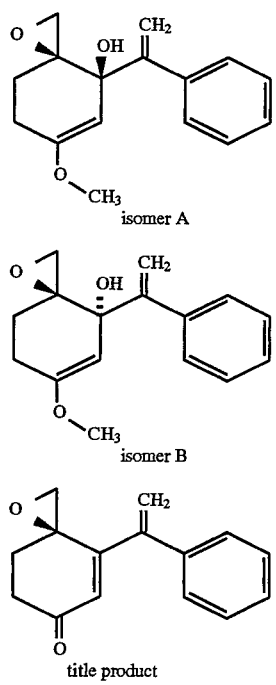

title product

Step B : 6-Hydroxy-4-(β-styryl)-1-oxa-spiro[2.5]oct-4-ene

By proceeding in accordance with the method of operation described in Step D of Example 1, starting from 0.16 g (0.71 mmol) of the compound obtained in Step A and 30 mg (0.75 mmol) of sodium borohydride in 22 ml of a dichloromethane/methanol mixture (10:1), 0.14 g (0.61 mmol) of the expected compound is obtained after chromatography on silica gel (eluant: heptane/ethyl acetate, 1:1).

Yield: 87%

Step C: 6-Chloroacetylcarbamoyloxy-4-(β-styryl)-1-oxa-spiro[2.5]oct-4-ene

By proceeding in accordance with the method of operation described in Step E of Example 1, starting from 0.14 g (0.61 mmol) of the compound obtained in Step B and 0.1 ml (1.14 mmol) of chloroacetyl isocyanate in 10 ml of anhydrous dichloromethane, 0.25 g (0.73 mmol) of the expected compound is obtained.

EXAMPLE 15

6-Chloroacetylcarbamoyloxy-4-(2-phenyloxiran-2-yl)-1-oxa-spiro[2.5]oct-4-ene

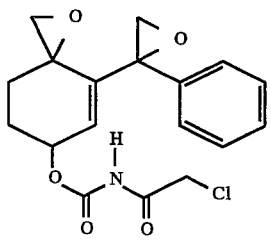

By proceeding in accordance with the method of operation described in Step C of Example 13, starting from 0.25 g (0.73 mmol) of the crude compound obtained in Example 14 in 25 ml of dimethyldioxirane, 90 mg (0.25 mmol) of the expected compound are obtained after chromatography on silica gel (eluant: heptane/ethyl acetate, 2:1).

Yield: 39%

Elemental analysis:
(Empirical formula: $C_{18}H_{18}ClNO_5$ molecular weight: 363.80)

|  | C | H | N |
|---|---|---|---|
| % found | 59.21 | 4.98 | 3.84 |
| % calculated | 59.43 | 4.99 | 3.85 |

EXAMPLE 16

(1S*,2S*,5S*,6S*)-5-Chloroacetylcarbamoyloxy-1-isopropenyl-2-(2-spiro-oxiranyl)-7-oxabicyclo[4.1.0]heptane

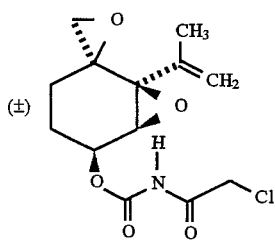

Step A: 5-Hydroxy-1-isopropenyl-2-(2-spiro-oxiranyl)-7-oxabicyclo[4.1.0]heptane

By proceeding in accordance with the method of operation described in Step D of Example 1, starting from 2 g (7.65 mmol) of 5-bromo-4-hydroxy-4-isopropenyl-1-oxaspiro[2.5]octan-6-one (isomer A) obtained as in Step C of Example 3 and 0.29 g (7.66 mmol) of sodium borohydride in 220 ml of a dichloromethane/methanol mixture (10:1), 0.69 g (3.79 mmol) of the expected isomer 1 and 1.2 g (6.59 mmol) of the expected isomer 2 are obtained after chromatography on silica gel (eluant: pentane/ethyl acetate, 4:1).

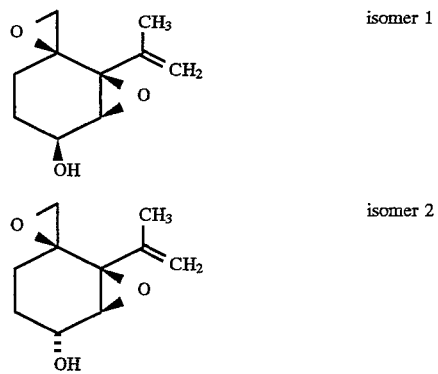

Step B: (1S*,2S*,5S*,6S*)-5-Chloroacetylcarbamoyloxy-1-isopropenyl-2-(2-spiro-oxiranyl)-7-oxabicyclo[4.1.0]heptane By proceeding in accordance with the method of operation described in Step E of Example 1, starting from 0.53 g (2.91 mmol) of isomer 1 obtained in the above Step A and 0.46 ml (5.41 mmol) of chloroacetyl isocyanate in 30 ml of anhydrous dichloromethane, 0.77 g (2.54 mmol) of the expected compound is obtained after chromatography on silica gel (eluant: heptane/ethyl acetate, 2:1).

Yield: 87%

Elemental analysis:
(Empirical formula: $C_{13}H_{16}ClNO_5$ molecular weight: 301.73)

|  | C | H | N | Cl |
|---|---|---|---|---|
| % found | 51.72 | 5.58 | 4.61 | 11.90 |
| % calculated | 51.75 | 5.35 | 4.64 | 11.75 |

That synthesis was carried out under the same operating conditions with isomer 2 obtained in Step A in order to obtain the compound of Example 29.

EXAMPLE 17

(1R*,2S*,5S*,6S*)-5-Chloroacetylcarbamoyloxy-1-[(2S* and 2R*)-(2-methyloxiran-2-yl)]-2-(2-spiro-oxiranyl)-7-oxabicyclo[4.1.0]heptane

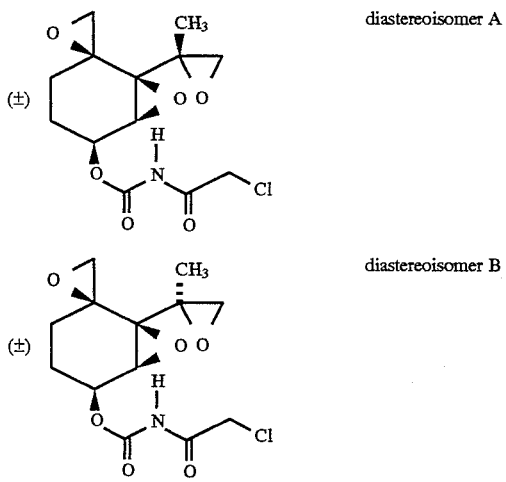

By proceeding in accordance with the method of operation described in Example 2, starting from 0.61 g (2.01 mmol) of the compound obtained in Example 16 and 1.96 g (16.1 mmol) of 72% 3-chloroperbenzoic acid in 50 ml of dichloromethane, 0.13 g (0.41 mmol) of diastereoisomer A and 0.08 g (0.25 mmol) of diastereoisomer B are obtained after chromatography on silica gel (eluant: heptane/ethyl acetate, 1:1) and HPLC on RP18 (eluant: acetonitrile/water, 20:80).

Yield: 32%

Elemental analysis of diastereoisomers A and B:
(Empirical formula: $C_{13}H_{16}ClNO_6$ molecular weight: 317.73)

|  | C | H | N | Cl |
|---|---|---|---|---|
| Diastereoisomer A |  |  |  |  |
| % found | 49.10 | 5.04 | 4.36 | 11.21 |
| % calculated | 49.14 | 5.08 | 4.41 | 11.16 |
| Diastereoisomer B |  |  |  |  |
| % found | 49.18 | 4.98 | 4.48 | 11.52 |
| % calculated | 49.14 | 5.08 | 4.41 | 11.16 |

That synthesis was carried out under the same operating conditions starting from isomer 2 obtained in Example 16 in order to obtain the two diastereoisomers described in Example 30.

EXAMPLE 18

(1S*,2S*,5R*,6S*)-5-Chloroacetylcarbamoyloxy-2-(2-spiro-oxiranyl)-1-(5-phenyl-pentyl)-7-oxabicyclo[4.1.0]heptane

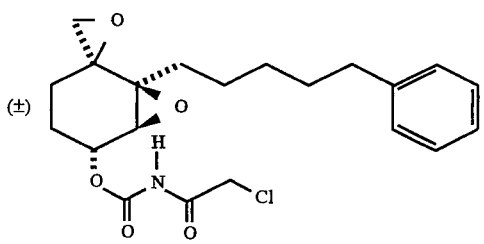

Step A: 5-hydroxy-2-(2-spiro-oxiranyl)-1-(5-phenylpentyl)-7-oxabicyclo[4.1.0]heptane By proceeding in accordance with the method of operation described in Step D of Example 1, starting from 4.2 g (11.5 mmol) of isomer C obtained in Step A of Example 10 and 0.22 g (5.8 mmol) of sodium borohydride in 440 ml of a dichloromethane/methanol mixture (10:1), 1.6 g (5.45 mmol) of the expected compound are obtained.

Step B: 5-Chloroacetylcarbamoyloxy-2-(2-spiro-oxiranyl)-1-(5-phenylpentyl)-7-oxabicyclo[4.1.0]heptane By proceeding in accordance with the method of operation described in Step E of Example 1, starting from 1.6 g (5.45 mmol) of the compound obtained in the above Step A and 0.85 ml (10.14 mmol) of chloroacetyl isocyanate, 0.16 g (0.39 mmol) of the expected compound is obtained after chromatogaphy on silica gel twice (eluant: heptane/ethyl acetate, 2:1).

Elemental analysis:
(Empirical formula: $C_{21}H_{26}ClNO_5$ molecular weight: 407.90)

|           | C     | H    | N    | Cl   |
|-----------|-------|------|------|------|
| % found   | 61.81 | 6.48 | 3.34 | 8.64 |
| % calculated | 61.84 | 6.42 | 3.43 | 8.69 |

EXAMPLE 19

(1S*,2R*,5R,*6S*)-2,5-Dichloroacetylcarbamoyloxy-2-methyl-1-(5-phenylpentyl)-7-oxabicyclo[4.1.0]heptane

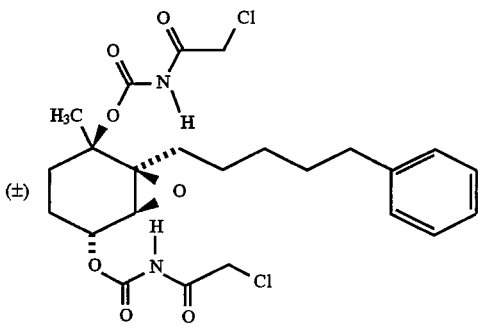

Step A: 2,5-Dihydroxy-2-methyl-1-(5-phenylpentyl)-7-oxabicyclo[4.1.0]heptane

By proceeding in accordance with the method of operation described in Step D of Example 1, starling from 4.2 g (11.5 mmol) of isomer E obtained in Step A of Example 10 and 0.22 g (5.8 mmol) of sodium borohydride in 440 ml of a dichloromethane/methanol mixture (10:1), 1.6 g (5.45 mmol) of the expected compound are obtained.

Step B: (1S*,2R*,5R*,6S*)-2,5-Dichloroacetylcarbamoyloxy-2-methyl-1-(5-phenylpentyl)-7-oxabicyclo[4.1.0]heptane By proceeding in accordance with the method of operation described in Step E of Example 1, starting from 1.6 g (5.45 mmol) of the compound obtained in the above Step A and 0.85 ml (10.14 mmol) of chloroacetyl isocyanate, 0.17 g (0.32 mmol) of the expected compound is obtained after chromatography on silica gel twice (eluant: heptane/ethyl acetate, 2:1).

Elemental analysis:
(Empirical formula: $C_{24}H_{30}Cl_2N_2O_7$ molecular weight: 529.42)

|           | C     | H    | N    | Cl    |
|-----------|-------|------|------|-------|
| % found   | 54.87 | 5.90 | 4.95 | 13.00 |
| % calculated | 54.45 | 5.71 | 5.29 | 13.39 |

EXAMPLE 20

6-Chloroacetylcarbamoyloxy-4-(4-methylpentyl)-1-oxa-spiro[2.5]oct-4-ene

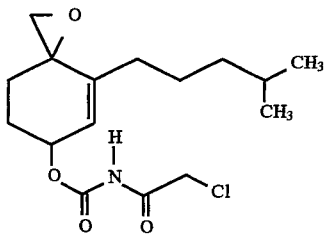

Step A: 4-(4-Methylpentyn-1-yl)-1-oxa-spiro[2.5]oct-4-en-6-one 16 ml (25.5 mmol) of n-butyllithium (1.6M in hexane) are added dropwise under a nitrogen atmosphere to a solution, cooled to −78° C., of 2 g (24.34 mmol) of 4-methylpentyne in 80 ml of anhydrous diethyl ether. The whole is stirred at −78° C. for 15 minutes and then at 0° C. for 50 minutes. There is then added dropwise to that solution a solution, cooled to −78° C., of 6-methoxy-1-oxa-spiro[2.5]oct-5-en-4-one (2.5 g; 16.21 mmol) in 30 ml of anhydrous toluene. After 1 hour's stirring at −78° C., the reaction mixture is poured into an aqueous 10% ammonium chloride solution. Conventional treatment of the organic phase yields after chromatography on silica gel (eluant: pentane/ethyl acetate, 4:1) 1 g (4.25 mmol) of isomer 1 and 1 g (4.25 mol) of a mixture of isomer 2 and transposition isomer 3, which is used in the following Step without being purified.

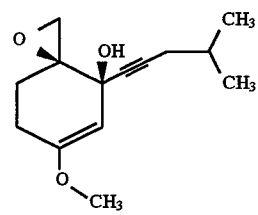

isomer 1

-continued isomer 2

[Structure: cyclohexene with O, OH, CH₃ branches, alkyne and isopropyl group, OCH₃]

isomer 3

[Structure: cyclohexenone with spiro-epoxide, alkyne, and isopropyl group]

Step B: 4-(4-Methylpentyl)-1-oxa-spiro[2.5]oct-4-en-6-one

Hydrogenation for 90 minutes, in the presence of 0.28 g of Lindlar catalyst, of a solution of 1 g (4.25 mmol) of the mixture of isomer 2 and isomer 3 obtained in Step A in 140 ml of benzene yields, after filtration and evaporation, 0.4 g (1.92 mmol) of the expected compound after chromatography on silica gel (eluant: pentane/ethyl acetate: 7:1).

Yield: 45%

Step C: 6-Hydroxy-4-(4-methylpentyl)-1-oxa-spiro[2.5]oct-4-ene

By proceeding in accordance with the method of operation described in Step D of Example 1, starting from 0.36 g (1.75 mmol) of the compound obtained in the above Step and 68 mg (1.8 mmol) of sodium borohydride in 55 ml of a dichloromethane/methanol mixture (10:1), 0.17 g (0.82 mmol) of the expected compound is obtained after chromatography on silica gel (eluant: heptane/ethyl acetate, 3:1).

Yield: 76%

Step D: 6-Chloroacetylcarbamoyloxy-4-(4-methylpentyl)-1-oxa-spiro[2.5]oct-4-ene

By proceeding in accordance with the method of operation described in Step E of Example 1, starting from 0.17 g (0.82 mmol) of the compound obtained in the above Step and 0.14 ml (1.55 mmol) of chloroacetyl isocyanate in 10 ml of anhydrous dichloromethane, 0.3 g (0.91 mmol) of the expected compound is obtained.

EXAMPLE 21

5-Chloroacetylcarbamoyloxy-2-(2-spiro-oxiranyl)-1-(4-methyl-pentyl)-7-oxabicyclo[4.1.0]heptane

[Structure diagram]

By proceeding in accordance with the method of operation described in Step C of Example 13, starting from 0.3 g (0.91 mmol) of the compound obtained in Example 20 in 20 ml of dimethyldioxirane, 22 mg (0.063 mmol) of the expected compound are obtained after chromatography on silica gel twice (eluant: toluene/ethyl acetate, 9:1).

Yield: 7%

Elemental analysis:
(Empirical formula: $C_{16}H_{24}ClNO_5$ molecular weight: 345.82)

|          | C     | H    | N    |
|----------|-------|------|------|
| % found  | 55.83 | 7.17 | 3.78 |
| % calculated | 55.57 | 7.00 | 4.05 |

EXAMPLE 22

**(3S*,4R*,5R*,6R*)-6-Chloroacetylcarbamoyloxy-4-isopropenyl-1-oxa-spiro[2.5]hexahydrobenzo[1.3]dioxol-2-one**

(±) [Structure diagram]

Step A: 4,5-Dihydroxy-4-isopropenyl-1-oxa-spiro[2.5]octan-6-one

By proceeding in accordance with the method of operation described in Step C of Example 13, starting from 1.8 g (9.2 mmol) of isomer B obtained in Step A of Example 3 in 100 ml of dimethyldioxirane, 1.7 g (8.6 mmol) of the expected compound are obtained after chromatography on silica gel (eluant: pentane/ethyl acetate, 4:1).

Yield: 93%

Step B: 4,5,6-Trihydroxy-4-isopropenyl-1-oxa-spiro[2.5]octane

By proceeding in accordance with the method of operation described in Step D of Example 1, starting from 0.59 g (2.98 mmol) of the compound obtained in the above Step and 0.11 g (2.98 mmol) of sodium borohydride in 66 ml of a dichloromethane/methanol mixture (10:1), 0.48 g (2.4 mmol) of the expected crude compound is obtained.

Yield: 80%

Step C: 5,6-Dichloroacetylcarbamoyloxy-4-hydroxy-4-isopropenyl-1-oxa-spiro[2.5]octane

By proceeding in accordance with the method of operation described in Step E of Example 1, starting from 0.48 g (2.4 mmol) of the crude compound obtained in the above Step and 0.76 ml (8.89 mmol) of chloroacetyl isocyanate in 40 ml of anhydrous dichloromethane, 1.3 g (2.96 mmol) of the expected crude compound are obtained.

**Step D: (3S*,4R*,5R*,6R*)-6-Chloroacetylcarbamoyloxy-4-isopropenyl-1-oxa-spiro[2.5]hexahydro-benzo[1.3]dioxol-2-one**

40 g of silica gel are added to a solution of 1.3 g (2.96 mmol) of the crude compound obtained in the above Step in 100 ml of dichloromethane. After 2 days' stirring at room temperature, the reaction mixture is filtered and then evaporated. After chromatography on silica gel (eluant: heptane/ethyl acetate, 2:1), 0.18 g (0.52 mmol) of the expected compound is obtained.

Yield: 18%

Elemental analysis:
(Empirical formula: $C_{14}H_{16}ClNO_7$ molecular weight: 345.74)

|  | C | H | N | Cl |
|---|---|---|---|---|
| % found | 49.08 | 4.99 | 3.82 | 10.06 |
| % calculated | 48.64 | 4.66 | 4.05 | 10.25 |

EXAMPLE 23

(3S*,4S*,5R*,6R*)-6-Chloroacetylcarbamoyloxy-4-(2-methyl-oxiran-2-yl)-1-oxa-spiro[2.8]benzo[1.3]dioxol-2-one

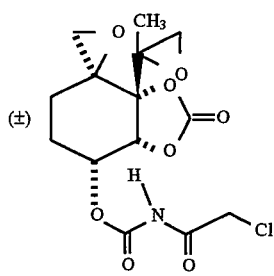

By proceeding in accordance with the method of operation described in Example 2, starting from 0.78 g (1.78 minor) of the crude compound obtained in Step D of Example 22 and 0.8 g (3.42mmol) of 72% 3-chloroperbenzoic acid, 0.1 g (0.28 mmol) of the expected compound is obtained after chromatography o silica gel twice (eluant: hexane/ethyl acetate, 1:1) and HPLC on RP18 (eluant: acetonitrile/water, 30:70).

Yield: 15%

Elemental analysis:
(Empirical formula: $C_{14}H_{16}ClNO_8$ molecular weight: 361.74)

|  | C | H | N |
|---|---|---|---|
| % found | 46.03 | 4.17 | 4.07 |
| % calculated | 46.49 | 4.46 | 3.87 |

The following three compounds were obtained in an analogous manner to the compounds of Examples 12, 27 and 28 respectively.

EXAMPLE 24 (1)

(3S*,4R*,6S*)-4,6-Dichloroacetylcarbamoyloxy-4-hexyl-1-oxa-spiro[2.5]octane

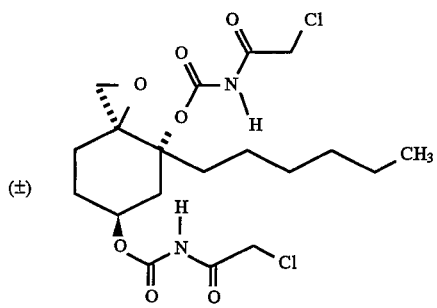

EXAMPLE 24 (2)

(3S*,4R*,6R*)-4,6-Dichloroacetylcarbamoyloxy-4-hexyl-1-oxa-spiro[2.5]octane

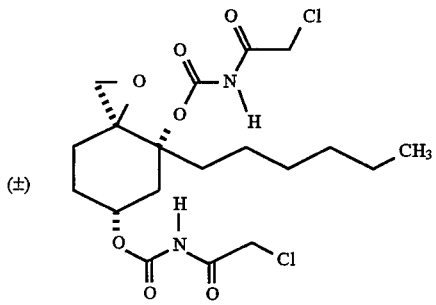

EXAMPLE 24 (3)

(3S*,4S*,6S*)-4,6-Dichloroacetylcarbamoyloxy-4-hexyl-1-oxa-spiro[2.5]octane

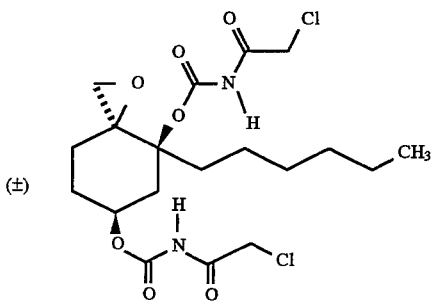

Elemental analysis:
(Empirical formula: $C_{19}H_{28}Cl_2N_2O_7$ molecular weight: 467.35)

|  | C | H | N |
|---|---|---|---|
| % found | 49.08 | 6.26 | 5.60 |
| % calculated | 48.83 | 6.04 | 5.99 |

Compounds 25(1) to 25(3) were also obtained in an identical manner.

EXAMPLE 25 (1)

(3S*,4S*,6S*)-4,6-Dichloroacetylcarbamoyloxy-4-isopropyl-1-oxa-spiro[2.5]octane

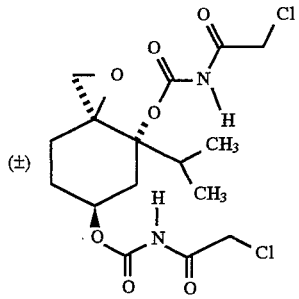

Elemental analysis:
(Empirical formula: $C_{16}H_{22}Cl_2N_2O_7$ molecular weight: 425.27)

|  | C | H | N |
|---|---|---|---|
| % found | 45.92 | 5.44 | 6.06 |
| % calculated | 45.19 | 5.21 | 6.59 |

EXAMPLE 25 (2)

(3S*,4S*,6R*)-4,6-Dichloroacetylcarbamoyloxy-4-isopropyl-1-oxa-spiro[2.5]octane

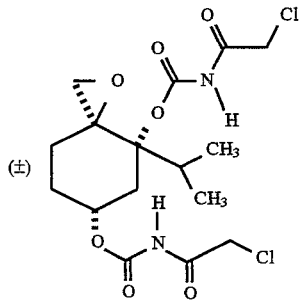

Elemental analysis:
(Empirical formula: $C_{16}H_{22}Cl_2N_2O_7$ molecular weight: 425.27)

|  | C | H | N |
|---|---|---|---|
| % found | 45.97 | 5.39 | 6.27 |
| % calculated | 45.19 | 5.21 | 6.59 |

EXAMPLE 25 (3)

(3S*,4R*,6S*)-4,6-Dichloroacetylcarbamoyloxy-4-isopropyl-1-oxa-spiro[2.5]octane

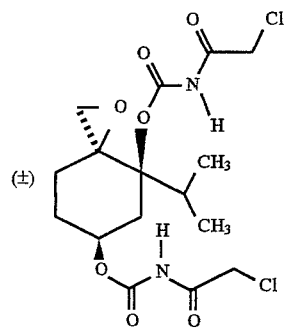

EXAMPLE 26

(3S*,4S*,6S*)-6-Chloroacetylcarbamoyloxy-4-hydroxy-4-(5-phenylpentyl)-1-oxa-spiro[2.5]octane

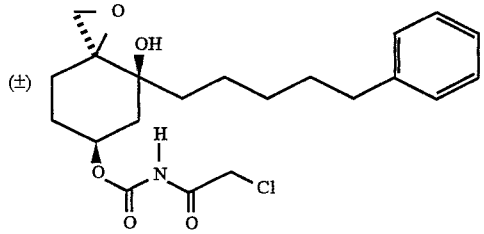

The title compound is obtained by proceeding as described for Example 11, but starting from isomer B obtained in Step B of Example 10.

Elemental analysis:
(Empirical formula: $C_{21}H_{28}ClNO_5$ molecular weight: 409.91)

|  | C | H | N |
|---|---|---|---|
| % found | 61.24 | 7.07 | 3.42 |
| % calculated | 61.53 | 6.89 | 3.42 |

EXAMPLE 27

(3S*,4R*,6R*)-4,6-Dichloroacetylcarbamoyloxy-4-(5-phenylpentyl)-1-oxa-spiro[2.5]octane

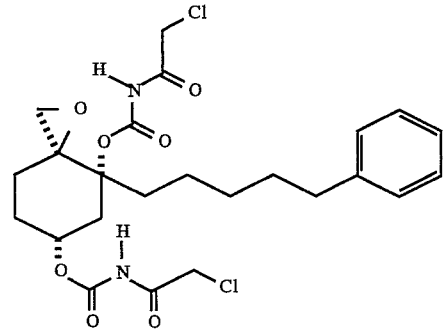

The title compound is obtained by proceeding as described for Example 12, starting from isomer A obtained in Step B of Example 10.

Elemental analysis:
(Empirical formula: $C_{24}H_{30}Cl_2N_2O_7$ molecular weight: 529.42)

|  | C | H | N | Cl |
|---|---|---|---|---|
| % found | 54.18 | 5.72 | 5.41 | 13.59 |
| % calculated | 54.45 | 5.71 | 5.29 | 13.39 |

EXAMPLE 28

(3S*,4S*6S*)-4,6-Dichloroacetylcarbamoyloxy-4-(5-phenylpentyl)-1-oxa-spiro[2.5]octane

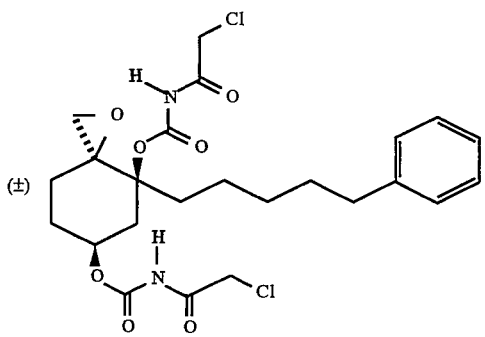

The title compound is obtained by proceeding as described for Example 12, starting from isomer B obtained in Step B of Example 10.

Elemental analysis:
(Empirical formula: $C_{24}H_{30}Cl_2N_2O_7$ molecular weight: 529.42)

|  | C | H | N |
|---|---|---|---|
| % found | 54.27 | 6.04 | 4.77 |
| % calculated | 54.45 | 5.71 | 5.29 |

EXAMPLE 29

(1S*,2S*,5R*,6S*)-5-Chloroacetylcarbamoyloxy-1-isopropenyl-2(2-spiro-oxiranyl)-7-oxabicyclo[4.1.0]heptane

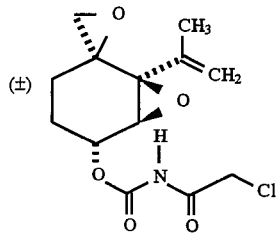

The title compound is obtained by proceeding as described in Example 16 starting from isomer 2.

Elemental analysis:
(Empirical formula: $C_{13}H_{16}ClNO_5$ molecular weight: 301.73)

|  | C | H | N | Cl |
|---|---|---|---|---|
| % found | 51.72 | 5.58 | 4.61 | 11.90 |
| % calculated | 51.75 | 5.35 | 4.64 | 11.75 |

EXAMPLE 30

(1R*,2S*,5R*,6S*)-5-Chloroacetylcarbamoyloxy-1-[(2S* and 2R*)-(2-methyloxiran-2-yl)]-2-(2-spiro-oxiranyl)-7-oxabicyclo[4.1.0]heptane

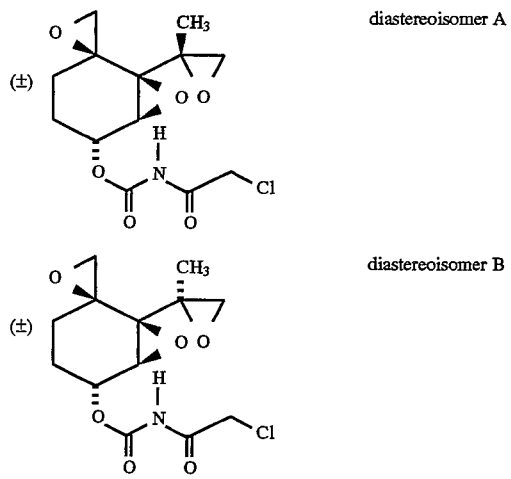

The two expected diastereoisomers are obtained by proceeding as described Example 17, but starting from isomer 2 of Example 16.

Mass spectrum: (molecular weight: 317) DCL ($NH_3$): $M+NH_4^+=335$

EXAMPLE 31

(3S*,4S*)-4-Chloroacetylcarbamoyloxy-4-(5-phenylpentyl)-1-oxa-spiro[2.5]octan-6-one

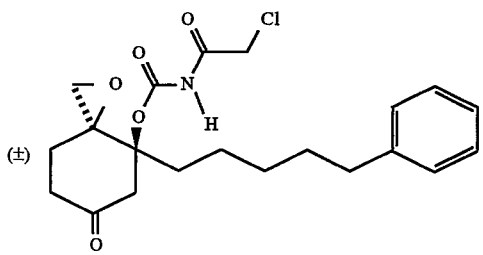

Step A: 4-Hydroxy-4(5-phenylpentyl)-1-oxa-spiro[2.5]octan-6-one

By proceeding in accordance with the method of operation described in Step A of Example 5, starting from 5.2 g (14.16 mmol) of the mixture of isomers C and D obtained in Step A of Example 10 in their ketonic form after the action of para-toluenesulphonic toluenesulphonic acid, and 5.8 ml (21.84 mmol) of tributyltin hydride in 75 ml of anhydrous toluene, 3.18 g (11.03 mmol) of the expected compound are obtained after chromatography on silica gel (eluant: pentane/ethyl acetate, 2:1).

Yield: 78%

Step B: (3S*,4S*)-4-Chloroacetylcarbamoyloxy-4-(5-phenylpentyl)-1-oxa-spiro[2.5]octan-6-one By proceeding in accordance with the method of operation described in Step E of Example 1, starting from 3.13 g (10.85 mmol) of the compound obtained in the above Step and 1.82 g (20.19 mmol) of chloroacetyl isocyanate in 100 ml of anhydrous dichloromethane, followed by purification by liquid phase chromatogragphy on silica RP 18 (eluant: acetonitrile/water, 575:425), 3.68 g (9.02 mmol) of the expected compound are obtained.

Yield: 83%

Elemental analysis:
(Empirical formula $C_{21}H_{26}ClNO_5$ molecular weight: 407.90)

|  | C | H | N |
|---|---|---|---|
| % found | 61.87 | 6.47 | 3.12 |
| % calculated | 61.84 | 6.42 | 3.43 |

EXAMPLE 32

(3S*,4R*)-4-Chloroacetylcarbamoyloxy-4-(5-phenylpentyl)-1-oxa-spiro[2.5]octan-6-one

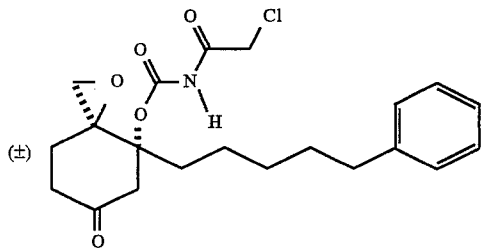

The title compound is obtained by proceeding as described for Example 31, but using the mixture of isomers A and B obtained in Step A of Example 10 in their ketonic form after the action of para-toluenesulphonic acid.

Elemental analysis:
(Empirical formula $C_{21}H_{26}ClNO_5$ molecular weight: 407.90)

|  | C | H | N |
|---|---|---|---|
| % found | 61.81 | 6.34 | 3.30 |
| % calculated | 61.84 | 6.42 | 3.43 |

EXAMPLE 33

4-(5-Phenylpentyl)-1-oxa-spiro[2.5]oct-4-en-6-one

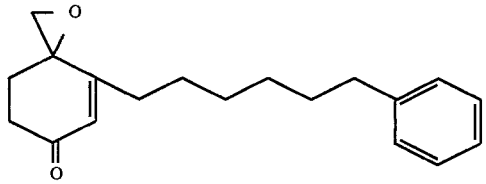

Treatment with magnesium sulphate, in solution in ethyl acetate, of the compound obtained in Example 32 yields the title compound.

Elemental analysis:
(Empirical formula $C_{18}H_{22}O_2$ molecular weight: 270.37)

|  | C | H |
|---|---|---|
| % found | 79.37 | 8.17 |
| % calculated | 79.96 | 8.20 |

EXAMPLE 34

(1S*,2S*,4S*)-1-Chloroacetylcarbamoyloxymethyl-4-chloroacetylcarbamoyloxy-2-(5-phenylpentyl)cyclohexane

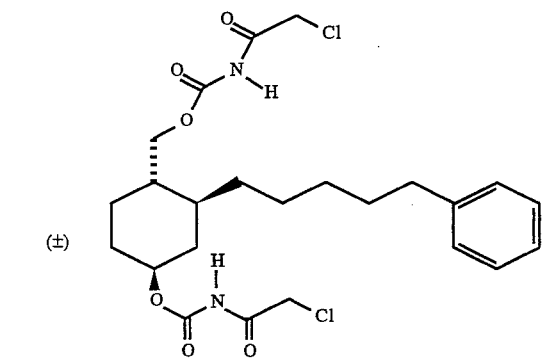

Step A: 4-Hydroxy-6-methoxy-4-(5-phenylpent-1-ynyl)-1-oxa-spiro[2.5]oct-5-ene

By proceeding in accordance with the method of operation described in Step A of Example 10, starting from 25 ml (0.157 mol) of 5-phenylpentyne in 600 ml of diethyl ether in the presence of 100 ml (0.150 mol) of n-butyllithium, and 15 g (0.097 mol) of 6-methoxy-1-oxa-spiro[2.5]oct-5-en-4-one in 80 ml of anhydrous toluene, 26.94 g of the expected compound are obtained.

Yield: 93%

Step B: 4-Hydroxymethyl-3-(5-phenylpentyl)cyclohex-2-enone

Hydrogenation of a solution of 24.9 g (83.45 mmol) of the compound obtained in the above Step in 1 I of benzene in the presence of 7.5 g of Pearlmann catalyst for 75 minutes yields, after filtration and evaporation of the solvent, 9.67 g (35.50 mmol) of the expected product and 2.83 g (10.46 mmol) of 4-(5-phenylpentyl)-1-oxa-spiro[2.5]oct-4-en-5-one, after chromatography on silica gel (eluant: heptane/ethyl acetate, 4:1).

Yield: 55%

Step C: 4-Hydroxymethyl-3-(5-phenylpentyl)cyclohex-2-enol (A and B) and 4-hydroxymethyl-3-(5-phenylpentyl)cyclohexanol (C)

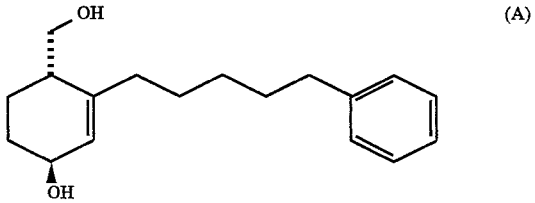

(A)

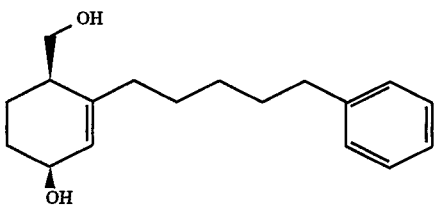

(B)

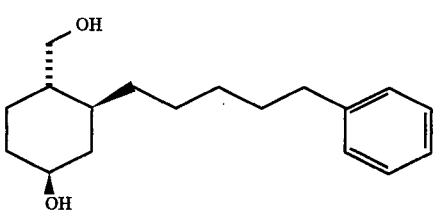

(C)

By proceeding in accordance with the method of operation described in Step D of Example 1, starting from 11.6 g (42.58 mmol) of the compound obtained in the above Step and 1.6 g (42.28 mmol) of sodium borohydride in 100 ml of a dichloromethane/methanol mixture (17:3), compounds A, B and C are obtained in the form of a mixture and are separated by chromatography on a silica column (eluant: toluene/ethyl acetate, 15:1) to yield:

A: 3.57 g (13.01 mmol)

B: 4.5 g (16.28 mmol)

C: 0.88 g (3.18 mmol)

Total yield: 76%

Step D: (1S*,2S*,4S*)-1-Chloroacetylcarbamoyloxymethyl-4-chloroacetylcarbamoyloxy-2-(5-phenylpentyl)cyclohexane By proceeding in accordance with the method of operation described in Step E of Example 1, starting from 0.7 g (2.5 mmol) of compound C obtained in the above Step in 25 ml of dichloromethane and 0.76 ml (5.96 mmol) of chloroacetyl isocyanate, conventional treatment of the organic phase, followed by precipitation in an ethyl acetate/pentane/diethyl ether mixture, 0.98 g (1.9 mmol) of the expected compound is obtained.

Yield: 75%

Elemental analysis:
(Empirical formula $C_{24}H_{32}Cl_2N_2O_6$ molecular weight: 515.44)

|  | C | H | N | Cl |
|---|---|---|---|---|
| % found | 55.31 | 6.28 | 5.33 | 13.69 |
| % calculated | 55.93 | 6.26 | 5.43 | 13.76 |

EXAMPLE 35

(1S*,4S*)-1-Chloroacetylcarbamoyloxymethyl-4-chloroacetylcarbamoyloxy-2-(5phenylpentyl) cyclohex-2-ene

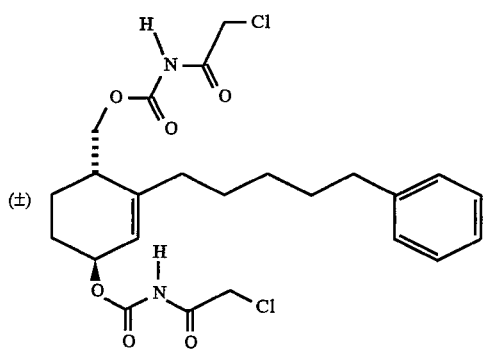

By proceeding in accordance with the method of operation described in the above Example, starting from 1 g (3.64 mmol) of compound A obtained in Step C of the above Example in 36 ml of dichloromethane and in the presence of 1.11 ml (13.56 mmol) of chloroacetyl isocyanate, 1 g (1.95 mmol) of the expected compound is obtained.

Yield: 53%

Elemental analysis:
(Empirical formula $C_{24}H_{30}Cl_2N_2O_6$ molecular weight: 513.42)

|  | C | H | N | Cl |
|---|---|---|---|---|
| % found | 56.11 | 6.04 | 5.42 | 14.14 |
| % calculated | 56.15 | 5.89 | 5.46 | 13.81 |

EXAMPLE 36

(1R*,4S*)-1-Chloroacetylcarbamoyloxymethyl-4-chloroacetylcarbamoyloxy-2-(5-phenylpentyl) cyclohex-2-ene

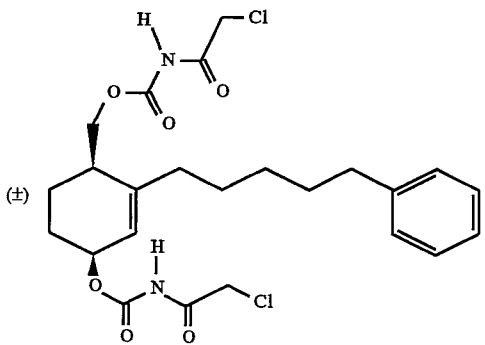

By proceeding in accordance with the method of operation described in the above Example, starting from 1.62 g (5.90 mmol) of compound B obtained in Step C of the above Example in 32 ml of dichloromethane and in the presence of 1.87 ml (21.96 mmol) of chloroacetyl isocyanate, 2.4 g (4.67 mmol) of the expected compound are obtained.

Yield: 80%

Elemental analysis:
(Empirical formula $C_{24}H_{30}Cl_2N_2O_6$ molecular weight: 513.42)

|  | C | H | N | Cl |
|---|---|---|---|---|
| % found | 56.27 | 5.89 | 5.45 | 13.99 |
| % calculated | 56.15 | 5.89 | 5.46 | 13.81 |

EXAMPLE 37

(2S*,5S*)-2-Chloroacetylcarbamoyloxymethyl-5-chloroacetylcarbamoyloxy-1-(5-phenylpentyl)-7-oxabicyclo[4.1.0]heptane

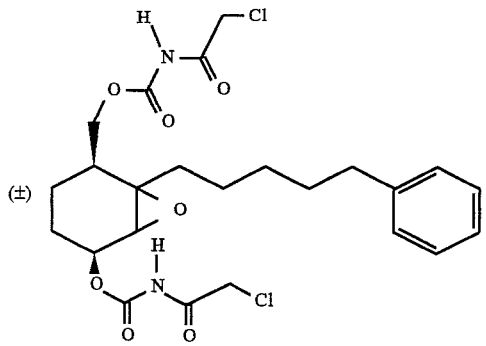

By proceeding in accordance with the method of operation described in Step C of Example 13, starting from 1 g (1.95 mmol) of the compound of Example 36 and 200 ml of dimethyldioxirane, 0.611 g (11.45 mmol) of the expected compound is obtained after reversed phase HPLC (grafted silica C18) (eluant: acetonitrile/water, 60:40).

Yield: 59%

Elemental analysis:
(Empirical formula $C_{24}H_{30}Cl_2N_2O_7$ molecular weight: 529.42)

|  | C | H | N | Cl |
|---|---|---|---|---|
| % found | 54.57 | 5.80 | 5.24 | 13.39 |
| % calculated | 54.45 | 5.71 | 5.29 | 13.39 |

EXAMPLE 38

(3S*,4S*,5R*,6S*)-5-Bromo-6-chloroacetylcarbamoyloxy-4-hydroxy-4-(2-methyl-2-oxiranyl)-1-oxa-spiro[2.5]octane

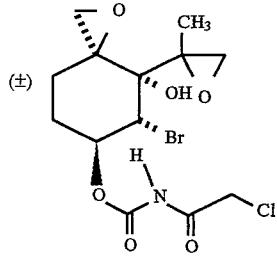

Diastereoisomer obtained in the course of the synthesis of the compound of Example 4.

Elemental analysis:
(Empirical formula $C_{13}H_{17}BrClNO_6$ molecular weight: 398.64)

|  | C | H | N |
|---|---|---|---|
| % found | 39.02 | 4.23 | 3.69 |
| % calculated | 39.17 | 4.30 | 3.51 |

EXAMPLE 39

(3S*,4S*,6R*)-4,6-Dichloroacetylcarbamoyloxy-4-(5-phenylpentyl)-1-oxa-spiro[2.5]octane

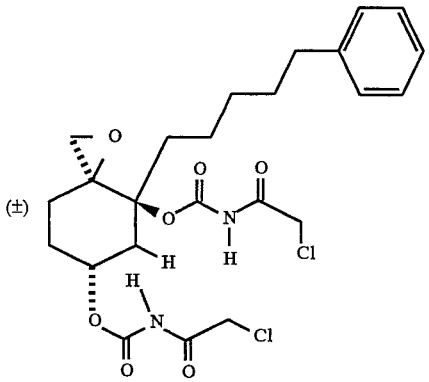

The title compound is obtained by proceeding as described for Example 12, starting from isomer D obtained in Step B of Example 10.

Elemental analysis:
(Empirical formula $C_{24}H_{30}Cl_2N_2O_7$ molecular weight: 529.42)

|  | C | H | N |
|---|---|---|---|
| % found | 54.25 | 5.94 | 5.47 |
| % calculated | 54.45 | 5.71 | 5.29 |

EXAMPLE 40

(3S*,4R*,6R*)-4,6-Di(2-chloropropanoyl)carbamoyloxy-4-(5-phenylpentyl)-1-oxa-spiro[2.5]octane

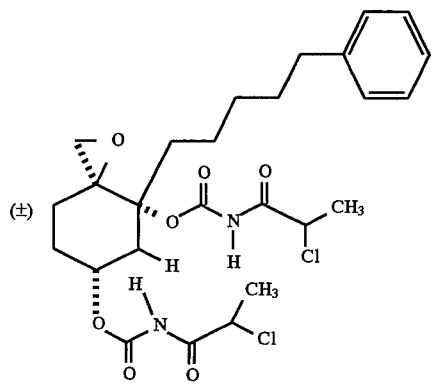

The title product is obtained by proceeding as described for Example 12, starting from isomer A obtained in Step B of Example 10, then replacing chloroacetyl isocyanate with 2-chloropropanoyl isocyanate.

EXAMPLE 41

Benzyl-[(1R*,4S*)-(1,4-dichlorocarbamoyloxy-2-(5-phenylpentyl)-cyclohex-2-enyl)methyl] methylsulphonium

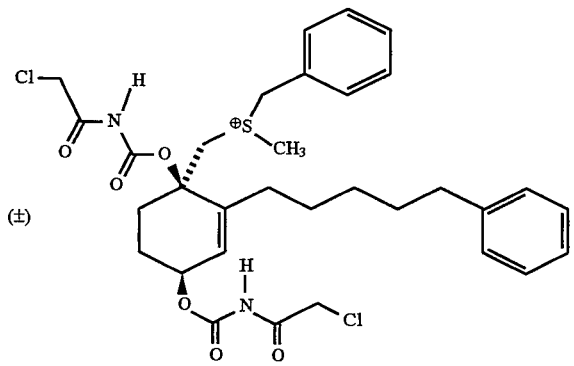

EXAMPLE 42

(3S*,4S*)-4-[(1E)-hex-1-enyl]-4-hydroxy-1-oxa-spiro[2.5]octan-6-one

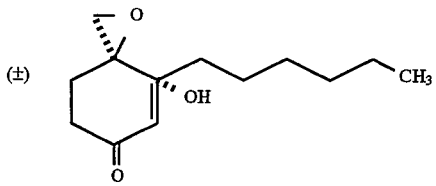

Step A: 4-(Hex-1-ynyl)-4-hydroxy-6-methoxy-1-oxa-spiro[2.5]oct-5-ene

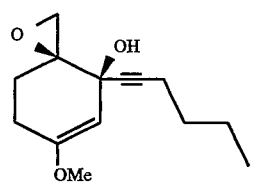
isomer 1

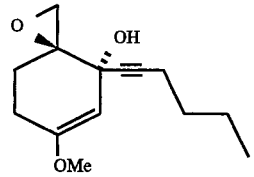
isomer 2

130 ml (207 mmol) of n-butyllithium (1.6M in hexane) are added dropwise, under a nitrogen atmosphere, to a solution, cooled to −78° C., of 17.16 g (208 mmol) of 1-hexyne in 800 ml of anhydrous diethyl ether. The whole is stirred at −78° C. for 15 minutes and then at 0° C. for 1 hour. There is then added dropwise to that solution a solution, cooled to −78° C., of 16 g of 6-methoxy-1-oxa-spiro[2.5]oct-5-en-4-one (104 mmol) in 100 ml of anhydrous toluene. After 4 hours' stirring at −78° C., the reaction mixture is poured into an aqueous 10% ammonium chloride solution. Conventional treatment of the organic phase yields, after chromatography on silica gel (eluant: pentane/ethyl acetate, 4:1), 10.4 g (44.01 mmol) of isomer 1 and 13 g (55.01 mmol) of isomer 2.

Yield: 95%

Step B: 4-(Hex-1-enyl)-4-hydroxy-6-methoxy-1-oxa-spiro[2.5]oct-5ene

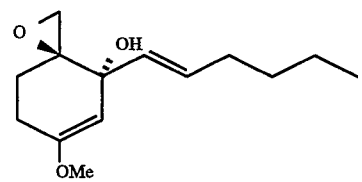
title product

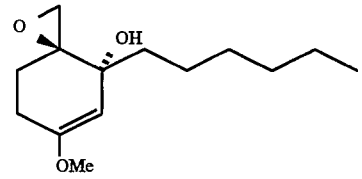
product α

Hydrogenation of a solution of 13 g (55.01 mmol) of isomer 2 obtained in Step A in 500 ml of benzene in the presence of 7.5 g of Lindlar catalyst for 7 hours yields, after filtration and concentration, 13 g (54.09 mmol) of a mixture of the title product and product α which is used in the following Step without being purified.

Step C: 5-Bromo-6,6-dimethoxy-4-(hex-1-enyl)-4-hydroxy-1-oxa-spiro[2.5]octane

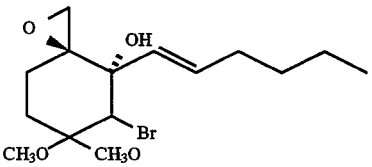
title product

-continued product β

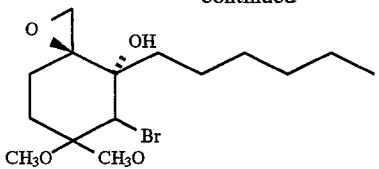

By proceeding in accordance with the method of operation described in Step B of Example 1, starting from 13 g (54.09 mmol) of the mixture of products obtained in Step B and 9.6 g (54.66 mmol) of N-bromosuccinimide in 500 ml of methanol, 17.3 g (49.25 mmol) of a mixture of the title product and product β is obtained, which mixture is used in the following Step without being purified.

Step D: 6,6-Dimethoxy-4-(hex-1-enyl)-4-hydroxy-1-oxa-spiro[2.5]octane title product product γ

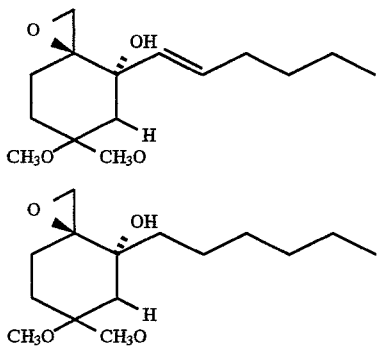

By proceeding in accordance with the method of operation described in Step A of Example 5, starting from 17.3 g (49.25 mmol) of the mixture of products obtained in Step C and 23.6 ml (88.89 mmol) of tributyltin hydride in 23.6 ml of anhydrous toluene, 13.4 g (49.56 mmol) of a mixture of the title product and product λ is obtained which is used in the following Step without being purified.

Step E: (3S*,4S*)-4-[(1E)-hex-1-enyl]-4-hydroxy-1-oxa-spiro[2.5]octan-6-one title product product δ

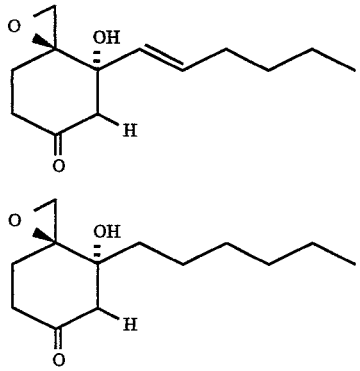

By proceeding in accordance with the method of operation described in Step C of Example 1, starting from 13.4 g (49.56 mmol) of the mixture of products obtained in Step D and 9.4 g (49.27 mmol) of para-toluenesulphonic acid in 500 ml of an acetone/water mixture (3:2), 1.19 g (5.3 mmol) of the title product and 1.7 g (7.51 mmol) of product δ are obtained after reversed phase chromatography (HPLC) (eluant: acetonitrile/water 40:60).

Yield: 11%

Elemental analysis:

| (Empirical formula: $C_{13}H_{20}O_3$ molecular weight: 224.30) | | |
|---|---|---|
| | C | H |
| % found | 68.93 | 8.96 |
| % calculated | 69.91 | 8.99 |

EXAMPLE 43

(3S*,4R*)-4-hexyl-4-hydroxy-1-oxa-spiro[2.5]octan-6-one

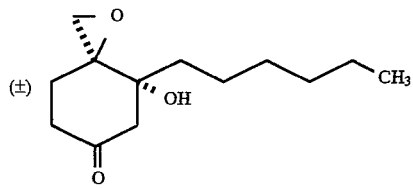

Product δ obtained in the course of the synthesis described in Example 42.

PHARMACOLOGICAL STUDY

Example A: Anti-Proliferative Study of the Compounds of the Invention

Three cell lines were used:
1 murine leukaemia L1210,
1 human epidermoid carcinoma, A431,
1 primary culture of pig aorta endothelial cells, CEAP.

The cells are cultured in RPMI 1640 complete culture medium containing 10% foetal calf serum, 2 mM glutamine, 50 units/ml of penicillin, 50 µg/ml of streptomycin and 10 mM HEPES (pH=7.4).

The cells are divided into microplates and exposed to the cytotoxic compounds. The cells are then incubated for two days (L1210), 3 days (CEAP) and 4 days (A431). The number of viable cells is then quantified by a colorimetric assay, the Microculture Tetrazolium Assay (Carmichael J., DeGraff W. G., Gazdar A. F., Minna J. D. and Mitchell J. R., Evaluation of a tetrazolium-based semiautomated colorimetric assay: assessment of chemosensitivity testing, Cancer Res., 47, 936–942, (1987)).

The compounds of the present invention demonstrated an anti-proliferative activity against those three cell lines.

By way of example, the $IC_{50}$s (concentrations of compound that inhibit by 50% the proliferation of the treated cells) are from 3 to 10 times lower than those of fumagillin, depending on the cell lines.

Example B: Inhibition of Neovascularization of Chicken Embryo Chorioallantoic Membrane This test was carried out with chicken embryos in the manner described above (Crum R., Szabo S. and Folkman J., Science, (1985), 230, 1375–1378). The fertilized eggs are incubated at 37° C. (D0). A pocket of air is created by removing 1 ml of albumin (D3), then a window is cut from the shell (D4) and the vitelline membrane is removed in order to separate the chorio-allantoic membrane (CAM).

The products to be tested are dissolved in ethanol and placed on methylcellulose disks which are dried and placed on the CAM on day 6. From 8 to 16 eggs are used per group. The zone situated round the disk is then examined 48 hours later. The eggs having an avascular zone greater than 4 mm in diameter are counted and the results are expressed as a percentage of eggs having an avascular zone. The results obtained for each of the compounds of the invention are indicated in the following Table 1:

TABLE 1

Inhibition of neovascularization of chicken embryo chorio-allantoic membrane

| Compound | % of eggs having an avascular zone |
|---|---|
| Example 6 | 79 ± 9 |
| Example 7 | 81 ± 10 |
| Example 10 | 73 ± 11 |
| Example 13 | 70 ± 16 |
| Example 17 Diastereoisomer A | 74 ± 7 |
| Example 18 | 69 ± 6 |
| Example 19 | 76 ± 9 |
| Example 21 | 76 ± 6 |
| Example 23 | 78 ± 7 |
| Example 28 | 90 ± 4 |
| Example 29 | 66 ± 6 |
| Example 30 | |
| Diastereoisomer A | 75 ± 7 |
| Diastereoisomer B | 68 ± 5 |

Example C: Antitumour Activity

The antitumour activity of the compounds of the invention was studied in accordance with the protocol described by R. I. Geran et al, *Cancer Chemotherapy Reports*, (1972), Part 3, pages 3 et seq.

Mice were divided at random into treated groups (11 mice per group) and a control group of 40 mice.

Tumour fragments were implanted on day 0 (subcutaneous implant). The compounds to be tested were administered for 12 days (day 1 to day 12) by the i.p. route.

The average weight of the tumour was determined on day 13 after implantation. The percentage inhibition was calculated in accordance with the following formula:

$$\% \text{ inhibition} = 100 - \frac{\text{average weight of the tumour (treated group)}}{\text{average weight of the tumour (control group)}}$$

As an example, the compound of Example 27 gave the following results:

| Dose (mg/kg) | % inhibition |
|---|---|
| 30 | 56 |
| 60 | 82 |

Example D: Pharmaceutical Composition: Tablets

Formulation for the preparation of 1000 tablets each containing 50 mg of active ingredient

| Compound of Example 12 | 50 g |
|---|---|
| Wheat starch | 15 g |
| Maize starch | 15 g |
| Lactose | 65 g |
| Magnesium stearate | 2 g |
| Silica | 1 g |
| Hydroxypropyl cellulose | 2 g |

We claim:

1. A compound selected from those of formula (I):

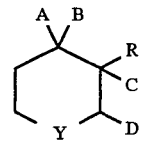

wherein:

R is selected from the radicals:

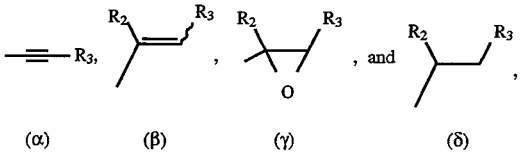

(α)    (β)    (γ)    (δ)

A and B are such that:
A and B, together with the carbon atom carrying them and with —CH$_2$—O—, form an oxirane ring, C and D are such that:
C represents hydroxy and D is selected from hydrogen and bromine, or,
and only when R represents (δ), C represents OR$_1$ and D is selected from hydrogen and bromine, or,
and only when R represents (δ), C and D each simultaneously represents hydrogen, or
C and D, together with the carbon atoms carrying them and with —O—, form an oxirane ring or, together with the carbon atoms carrying them and with —O—O(O)—O—, form a dioxygenated heterocycle, or C and D together form a bond, Y is selected from —O(O)— and —CH(OR$_1$)—, R$_1$ represents

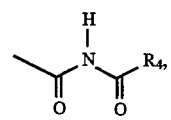

R$_2$ is selected from hydrogen, optionally substituted alkyl, and optionally substituted aryl, R$_3$ is selected from hydrogen, optionally substituted alkyl, and optionally substituted arylalkyl, R$_4$ is selected from optionally substituted alkyl, amino, optionally substituted alkylamino, optionally substituted dialkylamino, optionally substituted aryl, optionally substituted arylalkyl, optionally substituted heteroarylalkyl, and optionally substituted alkenyl, R$_5$ represents optionally substituted alkyl, R$_6$ is selected from optionally substituted alkyl, optionally substituted aryl, optionally substituted arylalkyl, optionally substituted heteroaryl, and optionally substituted heteroarylalkyl, it being understood that:

the alkyl chain in the terms "alkyl", "alkylamino", "dialkylamino", "arylalkyl" and "heteroarylalkyl" designates a saturated hydrocarbon chain having 1 to 6 carbon atoms inclusive in straight or branched chain, the term "aryl" designates a radical selected from phenyl and naphthyl, the term "heteroaryl" designates a radical selected from pyridyl, quinolyl, isoquinolyl, imidazolyl, indolyl, and isoindolyl, the term "alkenyl" designates a radical selected from vinyl and isopropenyl, the term "optionally substituted" associated with the radicals alkyl, alkylamino, dialkylamino, aryl, arylalkyl, heteroaryl, heteroarylalkyl, and alkenyl denotes that those radicals may optionally be substituted, in the acyclic moieties and/or, where applicable, in the cyclic moieties, by one or more chemical entities selected from:

hydroxy, halogen, selected from fluorine, chlorine, bromine, and iodine, trihalomethyl, nitro, amino, alkylamino, dialkylamino straight-chained or branched alkoxy having 1 to 6 carbon atoms inclusive, carboxy, straight-chained or branched alkoxycarbonyl having 1 to 6 carbon atoms inclusive, and straight-chained or branched acyl having 1 to 6 carbon atoms inclusive, and also the geometric isomers thereof, the diastereoisomers thereof and the enantiomers thereof, in pure form or in the form of a mixture.

2. A compound according to claim 1 wherein Y represents —CH(OR$_1$)—.

3. A compound according to claim 1 wherein Y represents —O(O)—.

4. A compound according to claim 1 selected from (3S, 4R,6R)-4,6-dichloroacetylcarbamoyloxy-4-(5-phenylpentyl)-1-oxa-spiro[2.5]octane, the (3S, 4R, 6S), (3S, 4S, 6R) and (3S,4S, 6S) diastereoisomers thereof, and the enantiomers thereof in pure form or in the form of a mixture.

5. A compound according to claim 1 that is (3S,4S,6S)-4,6-dichloroacetylcarbamoyloxy-4-hexyl-1-oxa-spiro[2.5]octane, the (3S,4S,6R), (3S,4R,6R) and (3S, 4R,6R) diastereoisomers thereof and also the enantiomers thereof in pure form or in the form of a mixture.

6. A compound according to claim 1 selected from (3S,4S, 6R)-4,6-dichloroacetylcarbamoyloxy-4-isopropyl-1-oxa-spiro[2.5]octane, the (3S,4S,6S), (3S,4R,6R) and (3S,4R, 6S) diastereoisomers thereof, and the enantiomers thereof in pure form or in the form of a mixture.

7. A compound according to claim 1 selected from 5-chloroacetylcarbamoyloxy-2-(2-spiro-oxiranyl)-1-(4-methylpentyl)-7-oxabicyclo[4.1.0]heptane, the diastereoisomers thereof, and the enantiomers thereof in pure form or in the form of a mixture.

8. A compound according to claim 1 selected from 5-bromo-6-chloroacetylcarbamoyloxy-4-hydroxy-4-(5-phenylpentyl)-1-oxa-spiro[2.5]octane, the diastereoisomers thereof and the enantiomers thereof, in pure form or in the form of a mixture.

9. A compound according to claim 1 selected from (3S, 4R)-4-chloroacetylcarbamoyloxy-4-(5-phenylpentyl)-1-oxa-spiro[2.5]octan-6-one, the (3S,4S) diastereoisomer thereof, and the enantiomers thereof in pure form or in the form of a mixture.

10. A method for treating a mammal afflicted with a disease requiring an angiogenesis inhibitor, comprising the step of administering to said mammal an amount of a compound of claim 1 which is effective for alleviation of said disease.

11. A pharmaceutical composition useful in inhibiting angiogenesis comprising an effective amount of a compound as claimed in claim 1, together with a pharmaceutically-acceptable excipient.

* * * * *

UNITED STATES PATENT AND TRADEMARK OFFICE
CERTIFICATE OF CORRECTION

PATENT NO. : 5,648,382
DATED : July 15, 1997
INVENTOR(S) : D. Billington, I. Picard, G. Atassi, A. Pierre, M. Burbridge, N. Guilbaud It is certified that error appears in the above-indentified patent and that said Letters Patent is hereby corrected as shown below:

Column 27, line 46: "after chromatography o silica gel" should read -- after chromatography on silica gel --.

Column 32, line 36: "as described Example 17," should read -- as described in Example 17 --.

Column 32, line 63: Delete "toluenesulphonic" (2nd instance).

Column 41, line 38: The letter Lambda ""  should read -- γ -- (the letter "Gamma).

Column 44, line 38: "-O-O(O)-O-," should read -- -O-C(O)-O- --.

Column 44, line 40: "-O(O)-" should read -- -C(O)- --.

Column 45, line 29: Insert a -- , -- (comma) after the word "thereof" (first instance).

Column 45, line 34: "-O(O)-" should read -- -C(O)- --.

UNITED STATES PATENT AND TRADEMARK OFFICE
CERTIFICATE OF CORRECTION

PATENT NO. : 5,648,382
DATED : July 15, 1997
INVENTOR(S) : D. Billington, I. Picard, G. Atassi, A. Pierre, M. Burbridge, N. Guilbaud It is certified that error appears in the above-indentified patent and that said Letters Patent is hereby corrected as shown below:

Column 46, line 3: Delete "that is" and replace with -- selected from --.

Column 46, line 6: Insert a -- , -- (comma) after the word "thereof" (first instance) and <u>delete</u> the word "also".

Column 46, line 20: Insert a -- , -- (comma) after the word "thereof" (first instance).

Signed and Sealed this

Fourth Day of November, 1997

*Attest:*

BRUCE LEHMAN

*Attesting Officer*   Commissioner of Patents and Trademarks